(12) United States Patent
Rol et al.

(10) Patent No.: US 8,110,182 B2
(45) Date of Patent: Feb. 7, 2012

(54) TREATMENT OF MULTIPLE SCLEROSIS BY ADMINISTRATION OF INTERFERON ALPHA AND C-PHYCOCYANIN

(75) Inventors: Giselle Penton Rol, Ciudad de la Habana (CU); Majel Cervantes Llanos, Ciudad de la Habana (CU); Eduardo Penton Arias, Ciudad de la Habana (CU); Diana Garcia del Barco Herrera, Ciudad de la Habana (CU); Carmen Maria Valenzuela Silva, Ciudad de la Habana (CU); Pedro Antonio Lopez Saura, Ciudad De la Habana (CU); Gerardo Enrique Guillen Nieto, Ciudad De la Habana (CU)

(73) Assignee: Centro de Ingenieria Genectica y Biotecnologia, Cuidad de La Habana (CU)

( * ) Notice: Subject to any disclaimer, the term of this patent is extended or adjusted under 35 U.S.C. 154(b) by 122 days.

(21) Appl. No.: 12/091,776

(22) PCT Filed: Oct. 30, 2006

(86) PCT No.: PCT/CU2006/000012
§ 371 (c)(1),
(2), (4) Date: Dec. 31, 2008

(87) PCT Pub. No.: WO2007/048357
PCT Pub. Date: May 3, 2007

(65) Prior Publication Data
US 2009/0280087 A1    Nov. 12, 2009

(30) Foreign Application Priority Data
Oct. 28, 2005  (CU) .................................. 2005-0207

(51) Int. Cl.
*A61K 38/20*   (2006.01)
*A61K 31/33*   (2006.01)
*C07K 14/56*   (2006.01)
*C07K 14/41*   (2006.01)

(52) U.S. Cl. ........ 424/85.7; 530/351; 530/370; 514/456
(58) Field of Classification Search ................ None
See application file for complete search history.

(56) References Cited

U.S. PATENT DOCUMENTS 5,163,898 A * 11/1992 Morcos et al. .................. 604/20

OTHER PUBLICATIONS

Jonasch E., et al. Interferon in oncological practice: Review of interferon biology, clinical applications, and toxicities. The Oncologist, 2001, vol. 6, p. 43-55.*
Remirez D, et al. Role of histamine in the inhibitory effects of phycocyanin in experimental models of allergic inflammatory response. Mediators of Inflammation, 2002, vol. 11, p. 81-85.*
Remirez D, et al. Effect of phycocyanin in zymosan-induced arthritis in mice—phycocyanin as an antiarthritic compound. Drug. Development Research, 1999, vol. 48, p. 70-75.*
Gonzalez R, et al. Anti-inflammatory activity of phycocyanin extract in acetic acid-induced colitis in rats. Pharmacological Research, 1999, vol. 39, No. 1, p. 55-59.*
Ito, R., et al. Interferon-gamma is causatively involved in experimental inflammatory bowel disease in mice. Clinical and Experimental Immunology, 2006, vol. 146, p. 330-338.*
Goldstein, D, et al. The role of interferon in cancer therapy: A current perspective. CA Cancer J. Clin., 1988, vol. 38, p. 258-277.*
van Holten J., et al. Treatment with recombinant interferon-beta reduces inflammation and slows cartilage destruction in the collagen-induced arthritis model of rheumatoid arthritis. Arthritis Research and Therapy, 2004, vol. 6, p. R238-R249.*

* cited by examiner

*Primary Examiner* — Robert Landsman
*Assistant Examiner* — Bruce D Hissong
(74) *Attorney, Agent, or Firm* — Hoffmann & Baron, LLP

(57) ABSTRACT

The present invention consists of the combination of Interferon alpha and C-Phycocyanin (IFN-α/C-Phyco) for obtaining a pharmaceutical preparation for autoimmune disease, allergy and cancer treatments. The anti-inflammatory, immunomodulator, antioxidant, anti-viral, anti-proliferative and anti-tumoral effects, associated to the regulatory T cell inducer effect demonstrated in this invention is the rationale for the use of the IFN-α/C-Phyco combination in these diseases.

6 Claims, 21 Drawing Sheets

Multiple Sclerosis Patient

Cells

IFN-α / C-Phyco

IFN-α

C-Phyco

Control

Cells

IFN-α / C-Phyco

IFN-α

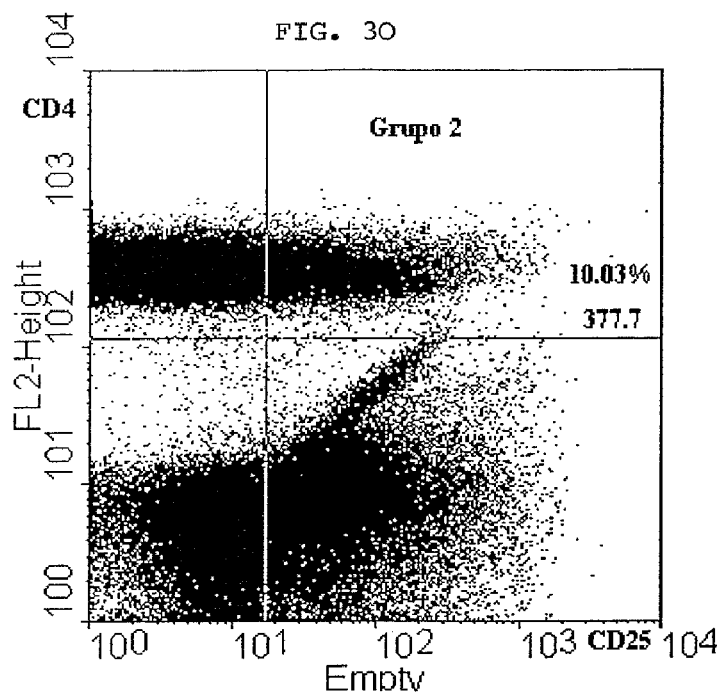
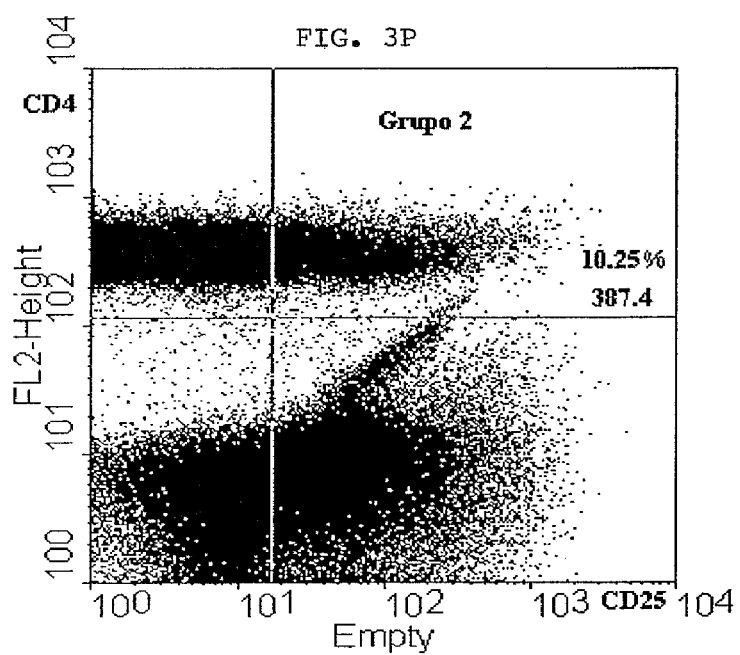
C-Phyco

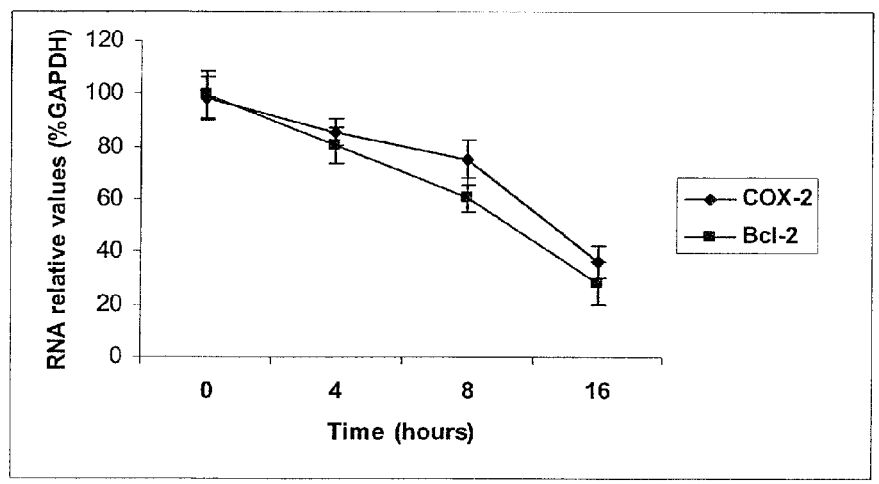
Figure 8
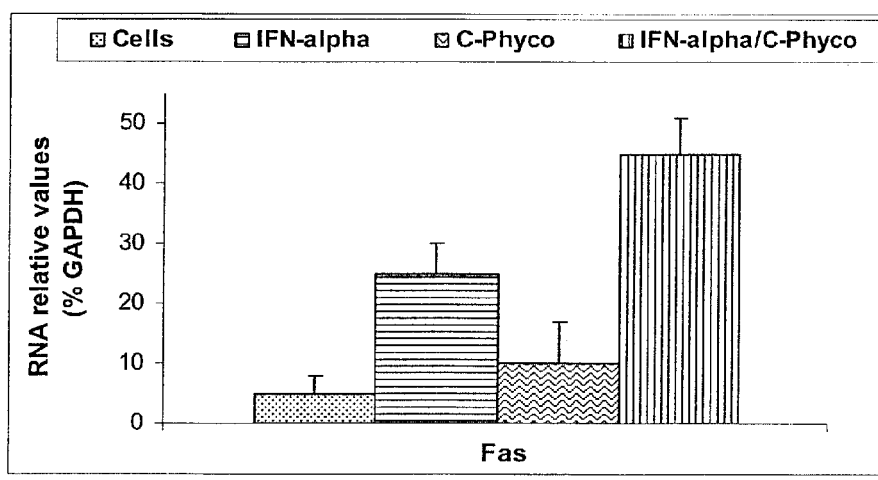

TREATMENT OF MULTIPLE SCLEROSIS BY ADMINISTRATION OF INTERFERON ALPHA AND C-PHYCOCYANIN

This application is the U.S. National Phase of, and Applicants claim priority from, International Application Number PCT/CU2006/000012 filed 30 Oct. 2006 and Cuban Application bearing Serial No. CU-2005-0207 filed 28 Oct. 2005, which are incorporated herein by reference.

FIELD OF THE INVENTION

The present invention is related to biological sciences, biotechnology and medical sciences, especially Neurology, Oncology, Internal Medicine and, in general, to the use of a combined therapy of known immunomodulator drugs, that are present as the active principles of natural products, for the treatment of autoimmune diseases, allergy and cancer. The invention is based on obtaining a pharmaceutical compound with anti-inflammatory, immunomodulatory, anti-oxidant, anti-viral, anti-proliferative and anti-tumoral effects, and particularly a regulatory T-cell induction effect that has been demonstrated in the present invention for the first time. It has a beneficial effect in autoimmune diseases (AD) such as multiple sclerosis (MS) and rheumatoid arthritis (RA), and in allergic diseases (ALD) such as bronchial asthma (BA), by reducing the number of relapses or crises in their recurrent clinical forms or detaining the progression in their monophasic clinical forms, while in cancer (CA) it stops the growth and proliferation of tumor cells, thus avoiding the progression of the tumor.

STATE OF THE PREVIOUS TECHNIQUE

Epidemiological studies have provided strong evidence on the increase of ALD and AD in developed countries during the last 3 decades. The incidence of these 2 types of diseases has increased: asthma (Woolcock A J, et al. Evidence for the increase in asthma worldwide. (1997) CIBA Found Symp 206: 122-134), rhinitis (Upton M N, et al. Intergenerational 20 years trends in the prevalence of asthma and hay fever in adults: The Midspan family study surveys of parents and offspring (2000) BMJ 321: 88-92) and atopic dermatitis (Williams H C. Is the prevalence of atopic dermatitis increasing? (1992) Clin Exp Dermatol 17: 385-391), representing ALD and MS (Rosati G, et al. Incidence of Multiple sclerosis in the town of Sassari, Sardinia, 1965 to 1985: evidence for increasing occurrence of the disease. (1988) Neurology 38: 384-388; Poser S, et at. Increasing incidence of MS in South Lower Saxony, Germany. (1989) Neuroepidemiology 8: 207-213), insulin-dependent diabetes mellitus (type I diabetes) (TID) particularly in young persons (EURODIAB ACE study group. Variation and trends in incidence of childhood diabetes in Europe. (2000) Lancet 355: 873-876) and Crohn's disease (Swarbrick E T, et al. A critical review of epidemiological studies in inflammatory bowel disease. (2001) Scand J Gastroenterol 36: 560a), as representatives of AD.

At the same time, there has been an evident decrease of the incidence of many infectious diseases in developed countries as a result of the use of antibiotics, vaccination or more simply, by improving sanitation and socioeconomic conditions.

The explanations for the increase of AD and ALD are basically related with genetic and environmental factors involved in their pathogenesis.

Regarding genetic factors, for example, in Japan, there is a low frequency of alleles DR3 and DR4-DQB1*0302 that increase the susceptibility to juvenile TID. Therefore the incidence of this disease is low, while the incidence of TID is high for Sardinian inhabitants (when compared with the neighboring regions), as well as in the direct descendants of Sardinian inhabitants who have migrated to continental Italy (Muntoni S, et at. Incidence of insulin-dependent diabetes mellitus among Sardinian-heritage children born in Lazio region, Italy. (1997) Lancet 349: 160-2).

The environmental factors could explain the rapid increase of AD and ALD in developed countries. There is information on the incidence of MS, TID and BA in populations that migrated from one country to another, which differ in the incidence of these diseases. The rate of development of TID in children of Pakistani origin who migrated to the United Kingdom is the same as that of the British children (11,7/100,000) or about 10 times higher than the incidence of TID in Pakistan (1/100,000) (Bodansky H J, et al. Evidence for an environmental effect in the aetiology of insulin dependent diabetes in a transmigratory population. (1992) BMJ 304: 1020-2). In Israel, MS is common in immigrants from Europe and infrequent in immigrants from Africa or Asia, in contrast, in native Israelites of European, Asian or African origin, the prevalence of MS is as high as in European immigrants (Leibowitz O R, et al. The changing frequency of multiple sclerosis in Israel. (1973) Arch Neurol 29: 107-10). It is also notable that the frequency of Systemic Lupus Erythematosus (SLE) is dramatically lower in persons from eastern African than in black Americans, two populations derived from the same ethnic group but exposed to different environments (Symmons D P M. Frequency of lupus in people of African origin (1995) Lupus 4: 176-8).

The influence of genetic and environmental factors on the susceptibility to AD and ALD must still be defined.

Important information comes from the incidence of these diseases in monozygotic twins. The proportion is of 25% for MS, (Murnford C J, et al. The British Isles survey of multiple sclerosis in twins. (1994) Neurology 44: 11-5), 40% for TID (Bach J F. Insulin-dependent diabetes mellitus as an autoimmune disease. (1994) Endocr Rev 15: 516-42) and 75% for asthma (Skadhauge L R, et al. Genetic and environmental influence on asthma: to population-based study of 11,688 Danish twin pairs. (1999). Eur Respir J 13. 8-14). It could be assumed that the agreement is directly related to the penetrance of the disease, with the condition that it is impossible to include in this analysis pairs of twins in which both twins have all the predisposing genes but are disease free. Important breakthroughs have recently occurred in the identification of chromosomal areas that include genes producing a predisposition of persons to MS (Oksenberg J R, et al. MS: genomic rewards. (2001) J Neuroimmunol 113: 171-84), TID (Todd J A. Genetics of type I diabetes. (1997) Pathol (Paris) 45: 219-27) and asthma (Cookson W O C. Asthma genetics. (2002) Chest 121: Suppl: 7S-13S), but very little information is available on the genes related to the disease, except for the HLA genes in AD. A crucial element is to identify which gene/genes directly modulate susceptibility that favor or protects us from environmental factors. An example is the observation in patients with atopic diseases in which the only polymorphism was found in the genes codifying for IL-10 and TGF-β (Hobbs K, et al. Interleukin-10 and transforming growth factor-beta promote polymorphisms in allergy and asthma. (1998) Am J Respir Crit Care Med 158: 1958-62), two cytokines that can contribute to the protective effect of infections on allergic diseases.

The development of most AD depend on IL-2 and IFN-γ cytokines produced by Th1 cells, while the development of allergic diseases requires IL-4 and IL-5, both produced by Th2 cells. The reciprocal feedback of Th1 cells for Th2 cytokines and of Th2 cells for Th1 cytokines, point to the fact that these cytokines may be involved in the protection mediated by infection against AD or ALD. In contrast to initial reports, (The EURODIAB Substudy 2 study group. Decreased prevalence of atopic diseases in children with diabetes. (2000) J Pediatr 137: 470-4) there is an association between AD and ALD in individual patients: the frequency of atopic diseases is increased in patient with diabetes and rheumatoid arthritis (Kero J, et at. TH1 and TH2 disease coexist? Evaluation of asthma incidence in children with coeliac disease, type I diabetes, or rheumatoid arthritis: to register study. (2001) J Allergy Clin Immunol 108: 781-3; Simson C R, et al. Coincidence of immune-mediated diseases driven by Th1 and Th2 subsets suggest to common aetiology: to population-based study using computerized general practice dates. (2002) Clin Exp Allergy 32: 37-42). These observations endorse the concept of a common mechanism between autoimmunity and allergy.

Considerable attention has been devoted to CD4+ T cells that express the alpha chain of the IL-2 receptor (CD25), called regulatory T cells (rTc) since the depletion of these cells in healthy mice induces a polyautoimmune Syndrome (Assano M, et al. Autoimmune disease as a consequence of developmental abnormality of to T cell subpopulation. (1996) J Exp Med 184: 387-96). This observation endorses the importance of maintaining the levels and appropriate functioning of this cellular subset to avoid the generation of an AD.

The following detailed phenotypic characterization of these preventive autoimmune cells offers no doubt on the existence of T regulatory cells as crucial mediators of self tolerance in animal and human models.

Cells with regulatory properties can be divided into 2 types: natural rTc, which are those generated by the thymus, and induced rTc, which are those generated by antigenic stimulation under special conditions in the periphery, called 'Th3', 'Tr1' or 'adaptive regulatory cells' (Bluestone J A, et al. Natural versus adaptive regulatory T cells. (2003) Nat Rev Immunol 3: 253-257). Suppression mechanisms for the induced rTc are fundamentally through the secretion of cytokines such as IL-10 and TGF-β (Groux H. Type 1 T-regulatory cells: their role in the control of immune responses. (2003) Transplantation 75: 8S-12S), however, natural rTc preferentially uses cell to cell contact.

Sakaguchi et al. were the first to identify the CD5 molecule as a rTc marker (Sakaguchi S, et at. Organ-specific autoimmune diseases induced in mice by elimination of T cell subset: I. Evidence for the active participation of T cells in natural self-tolerance; deficit of to T cell subset as to possible causes of autoimmune disease. (1985) J Exp Med 161: 72-87), while CD45RB was identified as another rTc marker (Powrie F, et at. Phenotypically distinct subsets of CD4+ T cells induces or Project from chronic intestinal inflammation in C. B-17 scid mice. (1993) Int Immunol 5. 1461-1471).

The main surface marker now used is CD25, (Sakaguchi S, et al. Immunologic self-tolerance maintained by activated T cells expressing IL-2 receiving alpha chains (CD25). Breakdown of to it sails mechanism of self-tolerance you cause various autoimmune diseases. (1995) J Immunol 155: 1151-1164). In mice, about 5-10% of the CD4+ cells and 1% of the CD8+ cells express $CD5^{high}$ and $CD45RB^{low}$, (Itoh M, et al. Thymus and autoimmunity: production of CD25+CD4+ naturally anergic and suppressive T cells as to key function of the thymus in maintaining immunologic self-tolerance. (1999) J Immunol 162: 5317-5326), in human the rTc are of 6-10% of the CD4+ cells (Ng W F, et al. Human CD4+CD25+ cells: to naturally occurring population of regulatory T cells (2001) Blood 98: 2736-2744). The rTc show high levels of CD11a (LFA-1), CD44, CD54 (ICAM-1), and CD103 in the absence of apparent antigenic stimulation (McHugh R S, et at. CD4+CD25+ immunoregulatory T cells: gene expression analysis reveals the functional role of the glucocorticoid-induced TNF receptor. (2002) Immunity 16: 311-323). Additionally rTc expresses CD152 (CTLA-4), a molecule solely expressed after cellular activation (Takahashi T, et al. Immunologic self-tolerance maintained by CD25+CD4+ regulatory T cells constitutively expressing cytotoxic T lymphocyte-associated antigen-4 (2000) J Exp Med 192: 303-310).

rTc expresses high levels of CCR5 chemokine receptors and their counterparts in humans (CCR4 and CCR8) (Bystry R S, et al. B cells and professional APCs recruit regulatory T cells via CCL4. (2001) Nat Immunol 2: 1126-1132). This distinctive pattern of chemokine receptor expression suggests that rTc can be rapidly recruited toward the inflammation areas and control the immune response efficiently. Many groups have reported expression of the glucocorticoid induced tumor necrosis factor receptor (GITR) in CD4+ CD25+ cells (McHugh R S, et al. CD4+CD25+ immunoregulatory T cells: gene expression analysis reveals to functional role for the glucocorticoid-induced TNF receptor. (2002) Immunity 16: 311-323).

The fact that rTr markers are also found in activated cells hinders their isolation and the identification of the CD25 as the marker of suppressor cells (Shevach E M. CD4+CD25+ suppressor T cells: More questions than answers. (2002) Nat Rev Immunol 2: 389-400).

Recent studies have shown that rTc is enriched in $CD25^{high}$ cells belonging to CD4+ T cells that express high levels of the alpha chain of the of IL-2 receptor. The $CD4+CD25^{high}$ T cells completely inhibit the proliferation and cytokine secretion of the CD4+ T cells. The $CD4+CD25^{high}$ T cells differ from CD4+CD25+ T cells in the expression levels of CD45RO and HLA-DR (Baecher-Allan C, et at. CD4+ $CD25^{high}$ regulatory cells in human peripheral blood. (2001) J Immunol 167: 1245-1253).

rTc derived from the thymus of mice and humans have been described. In mice, the absence of rTc produces organ-specific autoimmunity. Recently, it has been demonstrated that the transcriptional factor, Foxp3, is important for the functioning of the rTc in mice. It was shown that the expression of Foxp3 is typical of CD4+CD25+ T cells and is correlated with the suppressive activity of these cells. This suggests that the failure in rTc generation can contribute to AD and it also suggests that Foxp3 has a therapeutic role in the treatment of these diseases (Walker M R, et al. Induction of Foxp3 and acquisition of T regulatory activity by stimulated human CD4+CD25+ T cells. (2003) J Clin Invest 112: 1437-1443).

The Foxp3 transcriptional factor that codifies for the Scurfin protein seems to be a somewhat more exclusive marker of rTc (Brunkow M E, et at. Disruption of to new forkhead/winged-helix protein, scurfin, results in the fatal lymphoproliferative disorder of the scurfy mouse. (2001) Nat Genet 27: 68-73), although the possibility of expressing it is not excluded in other activation conditions and other cell populations (Morgan M E, et at. Expression of FOXP3 mRNA is not confined to CD4(+)CD25(+) T regulatory cells in humans. (2005) Hum Immunol. 1:13-20).

The action mechanism of induced rTc involved the TGF-β (Nakamura K, et at. Cell contact-dependent immuno-suppression by CD4(+)CD25(+) regulatory T cells is mediated by cell surface-bound transforming growth factor beta. (2001) J Exp Med 194: 629-44). The NK cells that have NK and T cell properties can contribute to this immunoregulation (Bendelac A, et al. Mouse CD1-specific NK1 T cells: development, specificity, and function (1997) Annu Rev Imunol 15: 535-62).

IL-10, Th2 cytokine, produced by induced rTc, monocytes and macrophages, slow down the progression of AD and ALD in experimental models (Moore K W, et at. Interleukin-10 and the receptor interleukin-10. (2001) Annu Rev Immunol 19: 683-765). IL-10 can also play an important role in ALD by decreasing the survival of the activated eosinophyls (Takanashi S, et at. Interleukin-10 inhibits lypopolisaccharide-induced survival and cytokine production by human peripheral blood eosinophils (1994) J Exp Med 180: 711-5). Two groups of researchers have found that there is a considerably lower amount of IL-10 in the lungs of asthma patients than in the lungs of the healthy controls (Lim S, et al. Haplotype associated with low interleukin-10 production in patients with severe asthma. (1998) Lancet 352: 113; Takan ashi S, et al. Interleukin-10 level in sputum is reduced in bronchial asthma, COPD and in smokers. (1999) Eur Resp J 14: 309-14).

This suggests that the IL-10 and TGF-β produced by the rTc can inhibit both responses (Th1 and Th2), thus being the mediators of this regulation.

The rTc play an important role in the control of the immune response, for example, they can limit the microorganism or anti-tumoral immune response. A strategic manipulation of rTc may be carried out to increase or diminish the immune response when required. (Fehérvari Z, et at. To paragon of self-tolerance: CD25+CD4+ regulatory T cells and the control of immune responses (2004) Arthritis Head Ther 6: 19-25).

The inductor effect of rTc of the IFN-α/Phycocyanin combination demonstrated in our invention justifies its use in AD and ALD where there is an imbalance of effector cells and rTc, with a decrease in the number and/or function of rTc.

Autoimmune diseases are dysfunctions of the immune system (IS) where the cells in charge of identifying and destroying harmful invading microorganisms, identify the self tissues as foreign and attack them. Researchers offer alternative explanations, such as viral or bacterial causes: Human Herpes virus 6, Epstein-Barr virus and the Clamydia pneumonia bacterium.

Infectious agents can induce AD under different experimental conditions, some of which have their clinical counterpart. Many mechanisms have been considered to explain these observations, including molecular mimicry and an increase in auto-antigen immunogenicity caused by inflammation in the target organ (Olson J K, et at. Virus-induced autoimmunity: potential role of viruses in initiation, perpetuation, and progression of T-cell mediated autoimmune disease. (2001) viral Immunol 14: 227-250). Paradoxically, infectious agents can also suppress autoimmune and allergic dysfunctions.

Experimental autoimmune encephalomyelitis (EAE) is a central nervous system (CNS) inflammatory and demyelinating disease that shows clinical and pathological characteristics that enable it to be considered the animal model of multiple sclerosis. A great deal of evidence show that EAE is a Th1 disease, with the secretion of pro-inflammatory cytokines such as interferon gamma (IFN-γ) or tumor necrosis factor-α (TNF-α) and it has been suggested that the oxidative stress induced by cytokines could play an important role in EAE neuropathology. However, the individual effects of these and other cytokines in the pathogenesis of diseases are still unknown. In this report, Mirror C et al. (Mirror C, et al. Interferon-gamma regulates oxidative stress during experimental autoimmune encephalomyelitis. (2002) Exp Neurol 177:21-31) analyzed the role of IFN-γ during EAE, using the receptor of IFN-γ knockout mice (IFN-gamma R (−/−)). The mice were immunized with the 40-55 peptide of rat myelin oligodendrocitic glycoprotein (MOG). The levels of oxidative stress were determined by the analysis of the immunoreactivity for the inducible syntase nitric oxide (NO), nitrotirosine and malonyldealdehyde, as well as through the expression of protective tissue antioxidant factors: metallotionein I+II (MT-I+II). They also determined the number of cells that develop apoptosis through of the use of the TUNNEL technique. The levels of oxidative stress, MT-I+II and apoptotic cell death by EAE was significantly increased in all mice (IFN-gamma R (−/−) and wild type), but it was even greater in IFN-gamma R (−/−) mice. This supports the hypothesis that IFN-γ plays a protective role against EAE.

EM is an autoimmune demyelinating disease basically affecting young adults. The most conservative value of MS incidence in Cuba is of 10/100,000 inhabitants (Hernandez-Valero E, et al. Clinical features of multiple sclerosis in Western Cuba. A comparison with two other regions in the country. (2004) Rev Neurol. May 1-15; 38(9):818-23).

It prevails in females with a proportion that varies according to the start of the disease. (Wingerchuk D M, et al. The clinical course of optic neuromyelitis (Devic's syndrome) (1999) Neurology 53: 1107-14). In regard to race, it is more frequent in whites.

MS is a CNS disease that affects the brain and spinal cord. It has 2 basic characteristics that are: demyelinization and axonal loss.

The symptoms, severity and clinical course may vary depending on the location of the plaques and the extent of the demyelination. It can therefore be classified in 2 main categories: the relapsing-remitting and the progressive chronic forms.

MS is referred to as an AD. Theoretically, this condition is developed when the immune system is damaged by genetic or environmental factors or both, causing the attack to self tissues. In the case of MS, the tissue is the myelin.

The organism also performs corrective events to "turn off" the effects of the destruction of myelin producing cells (oligodendrocytes). For example, it has been observed that there is an increase in the density of the sodium channels having electric loads that increase in number by which the nerve cells can continue communicating in spite of the loss of myelin; conversely, the nerves retain some remyelination capacity.

Multiple infectious organisms have been proposed as causative agents or co-factors in the development of MS (Johnson R T. Viral Possible causes of multiple sclerosis (1998) In: Viral infections of nervous system 2nd ed. Philadelphia: Lippincott-Raven 248-258), infections for HIV-1 (Blanche P, et al. Devic's neuromyelitis optic and HIV-1 infection (2000) J Neurol Neurosurg Psychiatry 68: 795-796) they were associated with the MS in autochthonous populations in this study. Endogenous retroviruses (ERV) have been involved in MS patogenesis and different groups have identified particular ERVs in association with MS (Perron H, et al. Molecular identification of to beginner retrovirus repeatedly isolated from patients with multiple sclerosis. (1997) The Collaborative Research Group multiple on Sclerosis. Proc Natl. Acad Sci USA 94: 7583-7588; Christensen T, et al. Reverse transcriptase activity and particle production in B lymphoblastoid cell lines established from lymphocytes of patients with multiple sclerosis. (1999) AIDS Head Hum Retroviruses 15: 285-291). This supports the use of drugs with antiviral properties in these diseases.

The cause of MS is unknown but there is a wide acceptance that it is an AD that is started by restricted MHC II CD4+ T cells that are polarized for the production of IFN-γ, IL-2 TNF-α and lymphotoxin, in other words, they are Th1 cells. Evidence shows that MS is an AD mediated by Th1 cells (CD4-Th1 model) (Lassmann H, et al. The CD4-Th1 model for multiple sclerosis: to crucial re-appraisal. (2004) Trend in Immunology 25: 3, 132-137). The realized predictions for this model are: a) CD4+ T cells should be predominant in the lymphocyte population of the MS lesion. Other populations of lymphocytes should be an accessory minority population. b) CD4+ T cells polarized to Th1 and their main effector cytokines, TNF-α and IFN-γ, should be pathogenic in the MS lesion. c) CD4+ T cells polarized to Th2 should be regulatory or anti-inflammatory in the MS lesion. The CD4-Th1 model should explain the variability observed in the clinical and pathological characteristics of MS. d) the process will be clearly autoimmune, this means that there must be evidence that the CNS of the host was not damaged before the autoimmune attack by CD4-Th1-mediated mechanisms.

In regard to the pathogenesis of MS, it has been postulated that in a genetically susceptible host, a common pathogen containing sequences that cross-react with the self myelin antigens, activates the antigen presenting cells (APC) through the Toll-like receptors (TLR), this is the minimum requirement for the induction of a CNS autoimmune inflammatory disease. The underlying immuno-regulatory defects, such as a decrease in regulatory T cells in the bloodstream of MS patients, lead to the final pathological activation of the auto-reactive T cells. The activated myelin reactive T cells migrate to the CNS and they recognize antigens presented by the microglia, local APCs. Th1 cytokines are secreted and the inflammatory cascade begins. The mechanisms that occur naturally can regulate the autoimmune response including the induction of Th2 cytokines secreted by T cells (IL-4, IL-5, IL-13), Th3 (TGF-β) or Tr1 (IL-10) that migrate to the CNS and negatively regulate the Th1 inflammatory auto-reactive T cells (Hafler D A. Multiple sclerosis (2004) J Clin Inv 113: 788-94).

Under normal conditions the blood brain barrier (BBB) provides an effective separation between the blood cells and myelin thus making it irrelevant if there were white cells that were programmed incorrectly, therefore, an inadequate function of the BBB during MS attacks has been postulated.

Some cells of the IS produce enzymes that dissolve the extracellular matrix. In most organisms this leads to a greater access of white cells to the infection area; however, when these cells release chemical substances in the capillary inside the CNS, there is a rupture of the BBB, producing a lesion, at least in certain individuals. One of the chemical substances that can be released by the white cells are the Metalloproteinases (MMPs) that weaken the between cell "cement". They are not in an active when they are released but they become activated by other enzymes (Maeda A, et al. Matrix Metalloproteinases in the normal human central nervous system, microglial nodules, Multiple and Sclerosis lesions (1996) J Neuropathol Exp Neurol. 55 (3): 300-309). Therefore, another characteristic of a potential treatment for these diseases would be the inhibition of MMPs and/or the stimulation of their inhibitors.

There is another potential mechanism affecting the integrity of the BBB. Thus, when the white cells destroy the invasive microorganisms, they release superoxides and free radicals that are extremely active and can destroy many of their targets, however, when the process occurs in the BBB, it starts producing a lesion, which can generate one or more attacks to the integrity of the BBB (Jean Claude Monboisse, et at. Non-enzymatic degradation of acid-soluble calf-skin collagen by superoxide ion: protective effects of flavonoids. (1983) Biochem Pharmacol. 32 (1): 53-58). Therefore, the antioxidant properties of the IFN-α/C-Phycocyanin combination demonstrated in our invention is the rationale of its use in this disease.

The MS plaques contain large amounts of macrophages which seem to destroy the myelin by digesting its proteins and lipids. The inhibitors of these enzymes can reduce the destruction of myelin or interfere in the movement of the macrophages toward the tissues. The principle of the drugs used in this disease to treat the acute conditions is based on its anti-inflammatory properties (W. A. Sibley and the Therapeutic Claims Committee of the International Federation Multiple of Sclerosis Societies, Therapeutic Claims in Multiple Sclerosis, 3rd Edition, 1992).

The therapies for the MS have emerged in the last 2 decades with the demonstration of the effectiveness of 3 types of immunomodulatory therapies that have an impact in the early stages of MS: immunosuppressor drugs such as Mitoxantrone and Ciclosfosfamide; Interferon Beta, and binding peptides to the Major Histocompatibility Complex (MHC) that are coupled to T cell receptors (TCR), Glatiramer Acetate (GA).

At present, the FDA approved drugs for this disease are Interferon Beta-1b (Betaseron) in 1993, Interferon Beta-1a (Avonex) in 1996 and Copaxone (GA or copolymer 1) in 1996 and they are very expensive.

IFN-β has had a great impact in relapsing-remitting MS, although we do not know if this can prevent the transition to a progressive secondary MS. The mechanism of action of the IFN-β is not clear. It probably involves alterations of a number of different mechanisms that include the induction of IL-10 and the inhibition of the movement of T cells by blocking the metalloproteinases (Stuve, O., et al. Interferon beta-1b decreases the migration of T lymphocytes in vitro: effects on matrix metalloproteinase-9 (1996) Ann. Neurol. 40:853-863). Clinical trials, based on the blocking the common p40 chain of IL-12 and IL-23, have now begun. These clinical trials also include the blocking of co-stimulatory signals through the interactions of B7-CD28 with Ig CTLA-4.

In regard to GA, in most patients a daily injection of GA produces the secretion of IL-5 and IL-13 for CD4+ T cells, indicating a change toward a Th2 response (Duda P W, et at. Human and murine CD4 T cell reactivity to complex antigen: recognition of the synthetic random polypeptide glatiramer acetate. (2000) J Immunol 65: 7300-7307; Qin, Y, et al. Characterization of T cell lines derived from glatiramer-acetate-treated multiple sclerosis patients. (2000) J Neuroimmunol 108: 201-206; Dabbert, D., et al. Glatiramer acetate (copolymer-1)-specific, human T cell lines: cytokine profile and suppression of T cell lines reactive against myelin basic protein. (2000) Neurosci. Lett 289: 205-208). Furthermore, the survival of T cells reactive to GA shows a high degree of degeneration, measured by its ability to cross-react with a large variety of peptides.

At present, there are original concepts that are now being discussed in Immunology, since they surpass the conventional precepts that limit the explanation of the evidence in conflict with the paradigm of clonal selection and its alternative, dominant tolerance, which is supported by the existence of regulatory T cells.

The therapeutic option given by our invention is focused, among other things, on reverting this effector/regulator imbalance that we believe plays an important role in autoimmune diseases through its capacity for increasing this cellular population: natural rTc CD4+CD25 high, Foxp3+ or induced rTc producers of IL-10 or TGF-β.

RA is another autoimmune inflammatory disease that produces a great handicap. It is considered that of the 50 to 90% of the persons affected by RA have severe disability 10 years after the first diagnosis (Markenson J A. (1991). Wordwide trends in the socioeconomic impact and long-term prognosis or rheumatoid arthritis. Semin Arthritis Rheum: 21(2), 4-12). The cost of the treatment and of the disability produced by RA in the United States is of up to 6.5 trillion dollars each year (Fanci A, et at (Ed) (1998). Harrison's principals of Internal Medicine. (14th ed.) (Chapter 376 p. 2412). New Cork: McGraw Hill; Yelin E. (1996). The cost of rheumatoid arthritis: absolute, incremental, and marginal estimates. J Rheumatol: (suppl 44)23, 47-51).

RA is the most common inflammatory arthritis and the main cause of disability, within the adult population of the world 0.5-1%.

RA is a poly-joint symmetrical inflammation that primarily affects the small joints of hands and feet. Besides the inflammation of the sinovium, the tissular mass called pannus, it invades and destroys the local joint structures. In RA, CD4+ T cells, B lymphocytes and macrophages infiltrate the sinovium and are sometimes organized as discreet lymphoid aggregates with germinal centers. The hyperplasia of the intima layer is the result of a marked increase in fibroblasts and macrophages type synoviocytes. Degrading enzymes expressed locally, include metalloproteinases, seric proteases and aggreganases, digest the sub-cellular matrix and destroy the jointstructure. (Firestein G S. Evolving concepts of rheumatoid arthritis (2003) Nature 423:356-61).

The pathogenesis of RA is as yet in general unknown; in particular, there are discussions on the role of autoimmunity against specific antigens of the joint structures. There is experimental evidence in favor of a multifactorial mechanism that includes genetic, infectious and neuroendocrin factors that lead to the prevalence of an antigen-specific activation of acquired immunity in the pathogenesis of the disease. The presence of HLA-DR4/Dw4 has been demonstrated in about 70% of Caucasian patients affected (Stastny P. Association of the B-cell alloantigen DRw4 with RA. (1978) N Engl J Med 298: 869-71).

In regard to the pathogenic mechanism, "epitope sharing" could act as the binding site for arthritogenic peptides or perhaps for the autoantigens that mimic an exogen antigen (molecular mimicry). Certain infectious agents have been proposed as the possible entities initiating RA (Feldmann M, et at. Role of cytokines in RA. (1996) Annu Rev Immunol 14: 397-440), particularly Parvovirus B 19 in which the ability of the virus to induce invasive properties in normal human synovial fibroblasts by changing their physiologic phenotype, has been demonstrated (Ray N B, et. al. Induction of an invasive phenotype by human parvovirus B19 in normal human synovial fibroblasts. (2001) Arthritis Rheum 44:1582-6).

Another important pathogen is Proteus mirabilis (Ebringer A, et al. Sequence similarity between HLA-DR1 and DR4 subtypes associated with RA and Proteus/Serratia membrane haemolysins. (1992) Ann Rheum Dis 51: 1245-6). Recently emphasis has been made on the direct role of innate immunity in the progression of the disease. The natural course of RA is characterized by 3 phases: induction, maintenance and tissue destruction. The advances in the knowledge on the molecules involved in the activation of T cells, the role of T cells in the erosion mechanism and the studies on the chemokines involved in the processes of "homing" and angiogenesis support the theory of an antigen-specific activation of the adaptive immune system. Therefore, during RA, the pathogenesis of synovitis and of erosions involve mechanisms both of the innate and adaptative immune system, thus producing the final induction of the joint damage (Valenisi G, Barone F, et at. Advances in immunology and rheumatoid arthritis pathogenesis. (2004) rheumatism 56: 9-20).

Recently, the development of biological agents used on molecules bound to membranes or to specific soluble mediators have revolutionized the treatment of RA. The success of the inhibition of TNF-α and, less significantly, that of IL-1, have provided firmly established therapies in the clinical management of RA. In spite of the data of the use of TNF-α inhibitors in clinical trials and in real life experience, a substantial proportion of patients do not respond to these agents or have lost their initial response to them, making it necessary to search for new therapies. Last year it was shown that B cell depletion using the monoclonal antibody Rituximab, produced a significant improvement in the symptoms and signs of the disease. At the same time, an improvement and an acceptable toxicity was found through the inhibition of the co-stimulation signal of T cells with the use of Ig CTLA-4. The selective IL-6 inhibition, a central pro-inflammatory cytokine in RA has produced clinical improvement in the condition of the disease, particularly in the acute response phase associated with RA (Singh R, et al. Emerging biologic therapies in rheumatoid arthritis: cell targets and cytokines. (2005) Curr Opin Rheumatol 17: 274-79).

Allergic diseases including allergic asthma, allergic rhinitis, foodborne allergies, allergy to drugs and the atopic allergic eczema/dermatitis syndrome and others, are a group of common dysfunctions which seem to be mediated by immunoglobulin E. People of all ages in any country of the world suffer from these diseases. The prevalence of allergies has increased in recent years. It affects 30-40% of the world's population and is considered one of the 3 major diseases of the XXI century.

In the last 2 decades, inflammation has been one of the main pathophysiologic characteristics of allergic reactions. Mastocytes are the main mediators of allergic reactions and their activation is a sufficient and necessary condition for the rapid development of microvasculature permeability and tissue edema in sensitive individuals exposed to allergens. Mastocytes are the main source of mediators of allergic inflammation that include: histamine, neutral proteinases, proteoglycans, prostaglandin D2, leukotriene C4 and certain cytokines (Parikh INC, et at. Preformed enzymes in mast cell granulates and their potential role in allergic rhinitis. (2003) Curr Asthma Rep 3: 266-272). Of these, histamines are the first mediators of the pathophysiologic changes involved in asthma.

Bronchial asthma is an expression of the chronic inflammation of the airway, possibly secondary to hypersensitivity to allergens. Hence, the treatment of this disease consists of environmental control in order to minimize the inflammatory response related to allergen stimulation, as well as the use of an antinflammatory therapy to reduce inflammation and prevent the progression of the disease (Craig M L. Diversity of asthma: evolving concepts of pathophysiology and lessons from genetics. (2005) J Allergy Clin Immunol 115: S526-31).

Asthma is endemic in developed countries and it can affect 1 out of every 4 children (Asher M I, Keil O R, et at. International study of asthma and allergies in childhood (ISAAC): rationale and methods. (1995) Eur Resp J 8: 483-91). Bronchial hyper-reactivity is found within the physiological framework of asthma but it also occurs in individuals without asthma (within 10-15% of the general population).

At present asthma is conceived as a disease produced by genetic-environmental interactions with a complex immunobiology. It begins early in life through the release of allergens into the airway. The first stage in the immune recognition of asthma occurs when the antigen enters the immune cells. The APC, including the dendritic cells, incorporate foreign proteins that can serve as antigens; they hydrolize them into small polypeptides, which can be expressed on their surface in the MHC class II context. This presentation is accompanied by the expression of accessory molecules on the surface of the APC. The process can occur near the surface of the airway and it is continued by the migration of these cells, having CCR7, toward the lymphoid tissue under the influence of the CCR7 ligands, EBI-1 and chemokines of the secondary lymphoid tissue, which also attract memory T cells and "naive" cells that have CCR7. The activation of the T cells takes place in the regional lymphoid tissue for the antigen loaded at the APC. The local expression of cytokines can have a deep effect on the response of T cells to antigen presentation, a process referred to as immune deviation. In the presence of IL-12 these cells have a Th1 phenotype that expresses IFN-γ. Under the influence of IL-10, these cells can develop a regulator phenotype that may be important in limiting the progression of asthma. The influence of IL-4 and IL-13 lead to the development of a Th2 phenotype that is required for the presence of asthma. Interestingly, the combined action of IL-4, IL-13, CD40 and an enzyme called citydin deaminase induced by activation produces a deletional change in the recombination of B lymphocytes and the production of specific IgE to allergens whose levels are increased in atopic asthma. It is this ability of the IgE to specifically bind to allergens and receptors on effector cells of the allergic response, including mastocytes, basophils and eosinophils, which lead to the release of the mediators causing asthma symptoms.

Effector molecules in asthma include histamine, an activating factor of platelets, proteases and metabolites of arachidonic acid (AA). Prostaglandins (PG) and leukotrienes (LT) are metabolites of AA enzymatically produced during allergic and asthmatic reactions and they are present in restricted places within the airway environment affecting the resident cells in the lungs while acting on specific receptors (Drazen J M. Leukotrienes in asthma. (2003) Adv Exp Med Biol 525: 1-5). The effector inflammatory cells in asthma produce leukotrienes, while the structural cells of the lung produce prostaglandins (Holgate S T, et al. Roles of cysteinyl leukotrienes in airway inflammation. (2003) J Allergy Clin Immunol 111 (suppl): S18-36).

The PG and LT can also be formed as a result of an oxidative stress. The activation of granulocytes of the respiratory tract that contain peroxidase is associated to the generation of oxidants at this level. When the formation of nitrogen and oxygen reactive species exceeds the reducing capacity of the environment of the respiratory tract, the peroxidation of lipid membranes can occur. This process leads to the isoprostane formation; these are markers of oxidative stress.

The availability of polymorphic markers and of phenotipically characterized families with several members suffering from asthma, has enabled the identification of genetic variants associated to the disease. The examination in populations from 12 studies of the genes that were suspected to be related with asthma (IL4, IL13, Tbet and GATA3) showed no correlation with the disease. The genes that have been associated to asthma include some well-known multifactorial genes such as desintegrin and metalloproteinase 33 (ADAM33) (Van Eerdewegh P, Little R D, et at. Association of the ADAM33 gene with asthma and bronchial hyperresponsiveness. (2002) Nature 418: 426-30), dipeptidil peptidasa 10 (DPP10) and PHD finger protein 11 (PHF11) (Zhang Y, et at. Positional cloning of to quantitative trait locus on chromosome 13q14 that influences immunoglobulin E levels and asthma. (2003) Nat Genet 34: 181-6). The mechanisms for which the variants of these genes affect the pathogenesis of asthma are now under study.

There is an emergent model in asthma pathogenesis. The traditional model for asthma was focused on the function of the smooth muscle in the respiratory tract and the inflammatory ways. Now, it incorporates the concept of the regulator system that affects cytokine and chemokine expression and it includes the effect of allergens on the growth and proliferation of resident cells in the airway (Holgate S T, et al. Roles of cysteinyl leukotrienes in airway inflammation. (2003) J Allergy Clin Immunol 111 (suppl): S18-36) which explains the role of the DP prostanoid receptor in asthma. In this model, the exposure to irritating agents, toxins or allergens, not only enables the deviation of the adaptative immune system and the recruitment of Th2 lymphocytes, eosinophils and mastocytes toward the airway, but it also acts indirectly in positioning the mastocytes near the cells of the smooth muscle of the respiratory tract (Brightling C E, et at. Mast-cell infiltration of airway smooth muscle in asthma. (2002) N Engl J Med 346: 1699-705) and activates the prostanoid DP receptor to promote its survival (Gervais F G, et at. Selective modulation of chemokinesis, degranulation, and apoptosis in eosinophils through the PGD2 receptors CRTH2 and DP. (2001) J Allergy Clin Immunol 108: 982-8). The repeated exposure to allergens produces changes in the activation condition of the epithelial cells of the airway and releases factors that cause the transformation of sub-epithelial fibroblasts into a collagen secretor myoblastic phenotype. The deposition of collagen on the basal membrane of the respiratory tract alters the constriction response of the smooth muscle of the airway affecting the lumen area (Wiggs B R, et at. A model of airway narrowing in asthma and in chronic obstructive pulmonary disease. (1992) Am Rev Resp Dis 145: 1251-8). The asthma symptoms are produced through the episodes of the release of pro-contractile mediators of eosinophils and mastocytes from the respiratory tract. The emergent concept is that asthma is a disease produced by infectious agents, allergens and environmental toxins that with the time lead to changes in cellular composition and airway structures.

Different subtypes of suppressive or regulatory T cells have been described in asthma that could prevent the "in vitro" and "in vivo" activation of effector cells in animal models. Recent evidence suggests a deficit in the suppressive activity of the CD4(+)CD25(+) natural regulatory T cells and the IL-10 producing regulatory T cells that can play a role in the development of allergic sensitization. The therapies should be targeted at maintaining the balance between regulatory T cells and effector cells in asthma (Robinson D S. The role of regulatory lymphocytes in asthma pathogenesis. (2005) Curr Allergy Asthma Rep 5: 135-41).

The models proposed about the tumorigenesis are based on the analysis of the characteristic main comuneses of the different types of cancer.

Recent studies (Karpinets V, et at. Tumorigenesis: the adaptation of mammalian cells to sustained stress environment by epigenetic alterations and succeeding matched mutations. (2005) Carcinogenesis 26: 1323-1334) indicate that during the tumorigenic transformations, the cells can generate their own mutations as a result of a tendency commit errors during cell division with the participation of polymerases that have a propensity to produce errors and aberrant mitosis. These mechanisms can be activated in cells by survival signalling and continued proliferation in a sustained stress environment (SSE): the long-term exposure to this signalling epigenetically re-programs the genome of certain cells and produces their senescence. The epigenetic re-programming results in: hypermethylation of the tumor suppressor genes involved in the initiation of the cell cycle arrest, DNA repair and apoptosis, proto-oncogen hypomethylation associated with persistent proliferative activity, global genome demethylation and activation of DNA repeated sequences.

According to this model, the persistent proliferation and signalling in a SSE can be originated by the continuous production of cytokines in a tissue exposed to permanent aggression, for example, as the result of carcinogen exposure. A signalling associated to a similar stress can be induced by other physiologic and environmental factors including very well-known cancer inducers as inflammation, hormones and viral infections.

The hormones involved in the origin and development of cancer is well documented. It is known that many hormones activate both the proliferative response and survival signalling in many cells, inducing their proliferation as well as apoptosis inhibition (Moggs J G, et al. Phenotypic anchoring of gene expression changes during estrogen-induced uterine growth. (2004) Environ Health Perspect 112: 1589-1606).

These issues are crucial for understanding how the regulation of the cell cycle and the apoptotic mechanism are important in the growth and development of neoplasms, which are signalling points that can result in the activation programmed cellular death paths if the cell damage cannot be repaired (Pietenpol J A, et al. Cell cycle checkpoint signalling: cell cycle arrest versus apoptosis. (2002) Toxicology 181-182: 475-481).

Studies have shown that the p53 and p21 are essential in maintaining the detention of the cell cycle at the G2/M phase and the apoptosis that follows DNA damage. The G2/M p53-dependent arrest mechanism involves an initial inhibition of the activity of the B1/Cdc2 cyclin for p21 and a subsequent reduction of the B1 and Cdc2 protein cyclin levels (Flatt P M, et at. p53 regulation of G(2) checkpoint i retinoblastoma protein dependent. (2000) Mol Cell Biol 20: 4210-23; Innocente INC, et at. p53 regulates to G2 checkpoint through cyclin B1. (1999) Proc Natl Acad Sci USA 96: 2147-52). Besides the modulation of the B1/Cdc2 cyclin levels and p21 activity, p53 also performs check-up responses through of the positive transcriptional regulation of additional target genes below the cascade (Chan T A, et at. 14-3-3 Sigma is required to prevent mitotic catastrophe after DNA damage. (1999) Nature 410: 616-20).

It has been reported that the induction of apoptosis is associated with the positive regulation of p53 target genes below the cascade, such as p21 (Kannan K, et al. DNA microarrays identification of primary and secondary target genes regulated by p53. (2001) Oncogene 20: 2225-2234).

The effects of transformant viruses on cellular processes mimic many aspects of the SSE. The oncoprotein expression coded by certain viruses changes the host cell processes in the same way as the survival and proliferative signal.

Approximately ¼ of the malignant diseases go through a phase of chronic inflammation (Coussens L M, et at. Inflammation and cancer (2002) Nature 420: 860-7). Similar to the SSE imposed for a carcinogen, this cellular environment leads to the production of oxygen reactive species as an important element in the system's cellular defence. Therefore, the inflammation, regardless of its aetiology, also causes a cellular aggression, DNA damage and produces a microenvironment that is rich in cytokines and growth factors that induce SSE.

There is much evidence sustaining the existence of a natural mechanism of immunologic surveillance against tumors that could be part of a more global process called "cancer inmuno-edition". This comprises the complete series of processes of the effects of innate and acquired immunity on tumor development that include from the recognition and tumor elimination to tumor escape (Dunn G P, et al. The Three is of cancer immunoediting: from immunosurveillance to tumor escapes. (2004) Annu Rev Immunol 22: 329-360). Surprisingly, tumors formed in the absence of an intact immune system are more immunogenic than those formed in the immunocompetent host; this reinforces the role of the immune system not only in the host's protection against tumor development but also, in its influence on the selection of tumoral variants on the basis of their immunogenicity.

Basically the lymphotoxic response of CD8+ T cells (CTL) to antigens presented in the MHC class I context is considered the main effector branch of acquired immunity in the anti-tumoral immune response, in this fashion, the major tendencies of the anti-tumoral immunotherapy are focussed on increasing the CTL response.

The theory of immunologic surveillance against the tumors undoubtedly demonstrates that the immune system is able to recognize and eliminate tumor cells.

One of the most relevant aspects in the mechanism of immunologic surveillance against tumors is the role of IFN-γ. The IFN-γ produced by the immune cell system is able to protect the host against the growth of transplanted tumors, as well as against the induction of chemo-induced and spontaneous tumors (Dighe A S, et at. Inhibition of cellular responsiveness to interferon-γ (IFN-γ) induced by overexpression of inactive forms of the IFN-γ receptor (1993) J Biol Chem 268: 10645-53). There is evidence supporting the previous statement, for example, the injection of monoclonal antibodies anti-IFN-γ in mice with transplanted tumors is shown to block their rejection induced by LPS; the transplanted fibrosarcoma grow faster and more efficiently in mice treated with monoclonal antibodies anti-IFN-γ, than in the non-treated mice; Knockout mice (−/−) IFN-γ R or (−/−) STAT1 were 10 to 20 times more sensitive to tumor induction by methylcholanthrene (MCA), than the control mice, by specifically developing more tumors, in less time and at a lower dose of MCA than the controls (Qin Z, et al. Inhibition of methylcholanthrene-induced carcinogenesis by an IFN-γ receptor dependent foreign body reaction. (2002) J Exp Med 195: 1479-90).

Tumor lines that are not sensitive IFN-γ grow much more than the sensitive ones. Tumor immune rejection is inhibited in a very similar way as in the Knockout mice. The tumor cell is the physiologic target of the IFN-γ in the rejection process in this experimental model. IFN-γ presents anti-proliferative and pro-apoptotic properties which have a direct effect on the tumor. The importance of the increase of IFN-γ dependent MHC I antigen presentation has been proven in similar models of tumor induction, as well as the importance of the induction of a Th1 response in generating an anti-tumoral response.

In relation to the rationale of using the two independent active principles that form part of the IFN-α/C-Fico combination, there is evidence suggesting a beneficial effect of type I IFNs (IFN-α e IFN-β) in MS.

Antiviral effect: Type I IFNs have a potent antiviral effect, they are induced after the cells are infected by viruses and they promote the synthesis of a large number of enzymes such as the 2'5'oligoadenilate synthetase that interferes in RNA or DNA virus replication. This early response (non-specific to the antigen) is crucial in limiting the extension of viral infection before the specific response to antigen is able to completely control the infection.

There are discrepancies in relation to the role of infections in MS predisposition, for example, Sieve et al. (Sieve A N, et al. Chronic restraint stress during early Theiler's virus infection exacerbates the subsequent demyelinating disease in SJL mice. (2004) J Neuroimmunol. October; 155 (1-2):103-18) in an animal model of demyelinating diseases in SJL mice demonstrated that the infection with Theiler's virus produced the enhancement of demyelinating events, in contrast, it has been reported that Schistosomiasis offers protection to MS in an EAE model, observing the direct suppression of the start of MS due to a Schistosoma mansoni infection (The Flamme AC, et al. Schistosomiasis protects against multiple sclerosis. (2004) Mem Inst Oswaldo Cruz; 99 (5 Suppl 1):33-6. Epub 2004 Oct. 13).

Anti-proliferative, anti-apoptotic and cell differentiation effects: The IFN-α and β can affect all cell cycle phases: M, G1 and G2. When fibroblasts are stimulated by the serum, the epidermal growth factor (EGF) or insulin, IFNs produces a prolongation of the G1 phase, a reduction in the rate of entrance to the S phase and slows down the S and G2 phases (Balkwill F, et al. Interferon affects both G1 and S+G2 in cells stimulated from quiescence to growth. (1978) Nature 274: 798-800; Gewert D R M G, et al. Inhibition of cell proliferation by interferons 1. Effects on cell division and DNA synthesis in human lymphoblasts (Daudi) cells (1984) Eur J Biochem 139: 619-625). The accumulative effect of the prolongation of the cell cycle by IFN in normal and tumoral cells produces cytostasis, an increase in cell volume and apoptosis (Otsuki T, et al. Human myeloma cell apoptosis induced by interferon-α. (1998) Br J Haematol 103: 518-529).

The tumor cells develop alterations in one or more proteins that will control the progression of the cell cycle. The proto-oncogens regulated by IFN include c-myc (Raveh T, et al. Double-stranded RNA-dependent protein kinase mediates c-Myc suppression induced by type I interferons. (1996) J Biol Chem 271: 25479-25484), bcl-2 (Koshiji M, et at. Apoptosis of colorectal adenocarcinoma (COLO201) by tumor necrosis factor-alpha and/or interferon-gamma resulting from down-regulation of Bcl-2 expression. (1998) Clin Exp Imunol 111: 211-218), c-Ha-ras (Samid D, et at. Biochemical correlates of phenotypic reversion in interferon-treated mouse cells transformed by to human oncogene. (1984) Biochem Biophys Res Comm 119. 21-28) and c-src. Another important mutated protein in many tumors is the retinoblastoma (Rb). The hyper-phosphorylation of this protein through its binding with the E2F transcriptional factor, inhibits the progression of the cell cycle; the treatment with IFN-α produces an inhibition of this hyper-phosphorylation (Kumar R, et al. Interferon-α induce the expression of retinoblastoma gene product in human Burkitt lymphoma Daudi cells: role in growth regulation. (1992) Proc Natl Acad Sci USA 89: 6599-6603; Resnitzky D, et al. Interferons and interleukin 6 suppress phosphorylation of the retinoblastoma protein in growth-sensitive hematopoietic cells. (1992) Proc Natl Acad Sci USA 89: 402-406). The IFN-α effect produces a reduction in the E2F, E2F-1 proteins.

One of the routes used in apoptosis induction involves the binding of Fas to FasL, which results in the recruitment of the protein containing the death domain, FADD and the consequent activation of caspases, such as caspase-8. IFNs positively regulate Fas expression and can therefore act through the Fas mediated apoptotic route (Weller M, et al. Anti-Fas/APO-1 antibody-mediated apoptosis of cultured human glioma cells. Induction and modulation of sensitivity by cytokines (1994) J Clin Invest 94: 954-964). Fas can be positively regulated by IFN-α, (Gordon M, et at. Treatment with interferon-alpha preferentially reduces the capacity for amplification of granulocyte-mecrophage progenitors (CFU-GM) from patients with chronic myeloid leukaemia but normal spares CFU-GM. (1998) J Clin Invest 102:710-715) and this event promotes the apoptosis mediated by Fas (Selleri C M J, et al. Fas-mediated modulation of bcr/abl in chronic myeloid leukaemia results in differential effects on apoptosis (1998) Blood 92: 981-989)

Genic modulation: The enzymes 2-5 oligoadenylate synthetase (2-5A synthetase), a protein kinase (PKR), and the indoleamine 2,3-dioxygenase (IDO) are induced by IFNs, the 2-5A synthetase is a relatively specific marker of IFN signalling (Hassel B A, et at. A dominant negative mutant of 2-5A-dependent RNase suppresses anti-proliferative and antiviral effects of interferon (1993) EMBO J 12: 3297-3304). The latent ribonuclease is activated by 2-5A; the induction of these enzymes can inhibit RNA and protein synthesis: The expression in cells of an enzymatically inactive ribonuclease (RNase-L) inhibits the anti-viral and anti-proliferative effects of IFNs. Apoptosis is suppressed in mice null-RNase-L treated with different apoptotic agents (Zhou A, et al. Interferon action and apoptosis are defective in mice devoid of 2',5'-oligoadenylate-dependent RNase 1 (1997) EMBO J 16: 6355-6363).

The levels of PKR are inversely correlated with proliferative activity in different human tumors and tumor cell lines, and a small PKR activity was found in invasive breast carcinoma (Haines G K C R, et al. Expression of the double-stranded RNA-dependent protein kinase (p68) in human breast tissues. (1996) Tumor Biol 17: 5-12; Savinova O J B, et al. Abnormal levels and minimal activity of the ds RNA-activated protein kinase, PKR, in breast carcinoma cells (1999) Int Biochem Cell Biol 31: 175-189).

The expression of PKR can be controlled by IRF-1, an IFN-induced transcriptional factor, since IRF-1 quickly increases in cells at a stage of arrest during growth, this can affect the expression of the genes involved in the negative control of cell growth and the IFN-mediated anti-proliferative effect. The degradation of tryptophan to quinurenin by IDO has also been related to the inhibition of protein synthesis and the anti-proliferative effect as a result of tryptophan depletion (Byrne G, et al. Induction of tryptophan degradation in vitro and in vivo: to gamma-interferon stimulated activity. (1986) J Interferon Res 6: 389-396).

IFNs also negatively regulate the multi-drug resistance gene (mdr1) in human cells of colon carcinoma (Stein U, et al. Modulation of mdr1 expression by cytokines in human colon carcinoma cells: an approach for reversal of multi-drug resistance. (1996) Br J Cancer 74: 1384-1391). The nucleotide arrays have demonstrated that the bcr gene (breakpoint cluster region) can also be regulated negatively by IFN-α (Der S D, et al. Identification of genes differentially regulated by interferon-α, β or γ using oligonucleotide arrays (1998) Proc Natl Acad Sci USA 95: 15623-15628).

Immunomodulator effect: The proportion of IFN-γ cell producers (Th1 cell types) increased in T cells cultivated in the presence of IFN-α and cloned (Parronchi P, et al. IL-4 and IFN alpha and IFN gamma exert opposite regulatory effects on the development of cytolytic potential by Th1 or Th2 human T cell clones. (1992) J Immunol 149: 2977-2983) or directly stimulated (Brinkmann V, et al. Interferon alpha increases the frequency of IFN gamma-producing CD4+ T cells (1993) J Exp Med 178: 1655-1663) through the TCR/CD3 complex route. Other reports demonstrate that IFN-α induces IFN-γ. In IFN-γ "knockout" mice an increment of the inflammation and demyelination has been observed (Tran E H, al. IFN-gamma shapes immune invasion of the central nervous system via regulation of chemokines. (2000) J Immunol 164: 2759-2768) which suggests the protective role of IFN-γ in demyelinating autoimmune diseases such as MS and its consequent beneficial role in diseases that show an increase in IFN-γ in contrast to the pathogenic pro-inflammatory role frequently assigned to it.

Effects on effector immune cells: IFNs increase the effectiveness of all cell types of immune effectors. These include cytotoxic T cells and natural killer cells (NK). Antibody-dependent cellular cytotoxicity (ADCC) can also be increased by IFNs. In addition to the enhanced expression of the molecules of human leukocitary antigens (HLA) IFNs directly increase the functions of relevant T cells for the cytotoxicity of tumoral cells (Kayagaki N, et al. Type I interferons regulate tumor necrosis factor-related apoptosis-inducing ligand (TRAIL) expression on human T cells: a novel mechanism for the anti-tumoral effects of type I Interferons (1999) J Exp Med 189: 1451-1460). The ability of IFNs to increase NK cell activity and their monocytic functions have been demonstrated in vitro and in vivo.

Angiogenesis effect: Another component of the IFN mediated anti-tumor effect is the inhibition of angiogenesis. The systemic administration of IFN-α reduces the growth rate of tumor cells in IFN sensitive cells, by the direct regulation of the angiogenic protein expression, bFGF (Dinney C P, et al Inhibition of Basic fibroblast growth factor expression, angiogenesis, and growth of human bladder carcinoma in mice (1998) Cancer Res 58: 808-814).

Clinically, the IFN-α treatment has been successful in the induction of hemangioma regression, which are tumors that contain abnormal endothelial cells (Ezekowitz R A B, et al. Interferon alpha-2b therapy for life-threatening hemangiomas of infancy (1992) N Engl J Med 326: 1456-1463). Kaposi's sarcoma, a neoplastic disease of endothelial origin also responds to the IFN-α treatment (Krown S E. Interferon-α: evolving therapy for AIDS-associated Kaposi sarcoma. (1998) J Interferon Cyto Res 18: 209-214).

Anti-tumoral effects of IFNs: It has been postulated that their anti-tumoral effects are either the result of the direct effect on the functional capacity or antigenic composition of tumor cell, or of an indirect effect on the modulation of the immune cell populations that interact with the tumor cell.

However, a certain number of type I IFN induced genes are involved in apoptosis and include PKR, PML, RAP46/Bag-1, phospholipid scramblase and the hypoxy inducible alpha-1 Factor (Der S D, et al. Identification of genes differentially regulated by interferon α, β or γ using oligonucleotide arrays. Proc Natl Acad Sci USA (1998); 95: 15623-15628). It would be important to determine if the IFNs effects in vivo could be increased by combining it with apoptosis inductor agents.

A recent study (Dunn G P, et at. A critical function for type I interferons in cancer immunoediting. (2005) Nature Immunol 6: 722-29) endorses the use of IFN type I (IFN α/β) in the treatment of tumors. This study identified IFN α/β as well as IFN-γ, as the crucial components in the cancer "inmunoedition" process. This group specifically demonstrates that in immunocompetent mice the endogenously produced IFNs α/β are required for the rejection of MCA sarcomas that are highly immunogenic, and also prevent the overgrowth of tumors induced by primary carcinogens since the host hematopoietic cells are critical targets of the IFN α/β during the development of the protective anti-tumoral response.

Human anti-tumor effects: IFNs have played an important role in clinical practice. The clinically beneficial therapeutic activity of IFN-α2 as a single agent has been demonstrated in many diseases. These discoveries endorse IFNs as the first human proteins to increase the survival of cancer patients. Combinations of IFNs with other drugs, have demonstrated encouraging results and new and more effective clinical applications. When combined with other therapies in animal models and cells, the IFNs have increased the effectiveness of the treatment in malignant diseases of diverse histology. The reduction in the number of cells or the size of the tumor and the prolongation of survival has had, in most cases, an additive or synergic effect.

Effect of IFNs on malignant hematological diseases: The degree of activity and the improvement in the quality of life of patients with hairy cell leukemia (HCL) led to the first license approved for an IFN in United States. More than 85% of the patients had objective evidence of partial or complete haematologic response to IFN-α2 (Quesada J, et al. Treatment of hairy cell leukemia with alpha interferon (1985) Blood 1986: 493-497).

In Chronic myeloid leukemia (CML), the application of IFN-α produced an important therapeutic response (more than 75%) in most of the newly diagnosed patients (Kantarjian H M, et al. Chronic myeloid leukemia: a concise update (1993) Blood 82: 691-703; Talpaz M. Use of interferon in the treatment of chronic myeloid leukemia. (1994) Semin Oncol 21: 3-7). The best results in CML have demonstrated a significant clinical response and a cytogenetic response with IFN-α2 (Talpaz M. Use of interferon in the treatment of chronic myeloid leukemia. (1994) Semin Oncol 21: 3-7). With a continuous treatment, approximately 25% of the patients have a complete cytogenetic response with the loss of the expression of the Philadelphia (Ph) chromosome. The average survival of responder patients showing evidence of a cytogenetic response (although not a complete response), is of approximately 6 years: more than 90% of those presenting a complete cytogenetic response have had remissions of more than 10 years. A mean survival of 10 years demonstrates a significant benefit for IFN-$\alpha_2$ compared to chemotherapy (leukemia TICSGoCM. Long-term follow-up of the Italian trial of interferon-alpha versus conventional chemotherapy in chronic myeloid leukemia. (1998) Blood 92: 1541-1548).

The myeloproliferative dysfunction associated to positive or negative thrombocytosis with the Ph chromosome, can be controlled with IFN-$\alpha_2$ (Ludwig H, et al. Treatment with recombinant IFNα-2c: multiple myeloma and thrombocythaemia in myeloproliferative diseases. (1985) Oncology 42 (suppl 1): 19-25; talpaz m, et al. Recombinant IFN-$\alpha_2$ therapy of chromosome-negative myeloproliferative disorders with thrombocytosis. (1989) Am J Med 86: 554-558).

Fifty percent of multiple myeloma patients that were not previously treated, have responded to the therapy with IFN-$\alpha_2$ (Quesada J R, et al: Collaborative phase I-II study of recombinant DNA-produced leukocyte interferon (clone A) in metastatic breast cancer, malignant lymphoma, and multiple myeloma (1984) Am J Med 77: 427-432).

IFN-α has had a therapeutic role in lymphomas of different histology and of T and B cell phenotypes, (Borden E C. Innovative treatment strategies for non-Hodgkin's lymphoma and multiple myeloma (1994) Sem Oncol 21: 14-22). IFN-$\alpha_2$ showed activity in 45% of the patients with advanced skin T cell lymphoma, with responses at 3 to 25 months (Borden E C. Innovative treatment strategies for non-Hodgkin's lymphoma and multiple myeloma (1994) Sem Oncol 21: 14-22). In lymphomas of poorly differentiated B cells, a frequency of response higher than 45% was found after the treatment with IFN-$\alpha_2$ (Foon K A, et al. Treatment of advanced non-Hodgkin's lymphoma with recombinant leukocyte ☐ interferon. (1984) N Engl J Med 311: 1148-1152; O'Connell M, Colgan J P, Oken M M, et al. Clinical trial of recombinant leukocyte A interferon as initial therapy for favorable histology non-Hodgkin's lymphomas and chronic lymphocytic leukaemia. An Eastern Cooperative Oncology Group pilot study. (1986) J Clin Oncol 4: 128-136)

Effect of IFNs on solid tumors: In the treatment of certain metastatic solid tumors, IFN-α resulted in an equivalent response to the best chemotherapeutic agents. The response of melanoma to IFN-α varies in a range between 2% and 29% (Creagan A N D, et al. Phase II study of recombinant leukocyte interferon (rIFN-alpha-A) in disseminated malignant melanoma. (1984) Cancer 54: 2844-2849; Robinson W, et al. Treatment of metastatic melanoma with recombinant interferon alpha 2. (1986) Immunobiology 172: 275-282). The combination of IFNs with hormones, chemotherapy and/or IL-2 could increase the response and prolong survival in metastatic melanoma although its integration as a therapy modality has been limited by their toxicities (Legha S S R S, et al. Development and results of bio-chemotherapy in metastatic melanoma: the University of Texas M.D. Anderson Cancer Center experience (1997) Cancer J Sci Am; 3 (suppl 1): S9-S15).

In metastatic renal carcinoma IFN-α, IFN-α+IL-2 combination, IFN-α+IFN-γ combination therapies have been used, but the results of a meta-analysis suggest that the patients that have been treated with IFN-α have better response than those treated with combined therapies, mainly due to their toxicity (Hemberg M, et al. Regimens with or without interferon-alpha as treatment for metastatic melanoma and renal cell carcinoma: an overview of randomized trials (1999) J Immunother 22: 145-154).

The bioactive substances of organic origin that exert regulatory roles in nature, constitute basic active principles that can act as drugs with therapeutic mechanism based on the development of the intrinsic curative potentials of the individual himself. This approach is based on the use of bio-regulatory products and procedures used to promote, to release or to stimulate the individual's capacities to achieve the restoration of the functional homeostatic balance altered in the disease. The rational use of these active principles and biological response modifiers has the objective of helping the patient to restore in a progressive and gradual way the regularity of the altered functions, through physiologic mechanisms and pathways.

Circumstantial or experimental evidence suggest the use of the potentially therapeutic properties of products of a natural or extractive origin, or plant derivatives. These bio-pharmaceutics can be complex mixtures of natural origin, or isolated components, concentrated or semi-purified in the industry that have the common characteristic of presenting one or several known or referred pharmacological activities of possible therapeutic application, this is the case of C-Phycocyanin (C-Phyco).

C-Phyco is a pigment bound to a protein found in green-blue algae. The C-Phyco monomers are linked to two different α and β protein subunits, containing at least three bilin chromophores covalently linked and an open tetrapyrrolic chains without metal complexes (Duerring M, et al. Isolation, crystallization, crystal structure análisis and refinement of constitutive c-phycocyanin from the chromatically adapting Cyanobacterium fremyella diplosiplon at 1.66 A resolution (1991). J Mol Biol; 217: 577-92). This prosthetic group accounts for around 4% of the algae mass, indicating the presence of approximately 16 chromophore groups per molecular weight unit (Oh Eocha C. Phycobilins. In: Lewin R A, editor. Physiology and Biochemistry of Algae: New Cork: Academy Press, 1962: 421-35). There are four different structural forms: monomeric, trimeric, hexameric and decameric (MacColl R, et al. Phycobiliproteins. Boca Ratón: CRC Press, 1987: 1-10), being the most abundant pigment in the blue-green algae (more than 20% of the alga dry weight) (Richmond A. Large scale microalgal culture and applications. In: Round Chapman, editors. Progress in Phycological Research. Vol. 7 Biopres Ltd., 1990:8).

The chemical structure of the bilin chromophores in C-Phyco, (open tetrapyrrolic chains) is very similar to bilirrubin. Stocker et al. (Stocker R, et al. Bilirrubin is an antioxidant of possible physiological importance (1987) Science; 235: 1043-6) reported that bilirrubin is a possible antioxidant of physiologic importance since it could eliminate peroxide radicals delivering them to an hydrogen atom bound to C-10 of the tetrapyrrolic molecule to form a radical with a central carbon with resonance stabilization that expands to the whole bilirrubin molecule. It is well-known that oxygen reactive species (ORS) are involved in diverse important processes in Medicine that include: inflammation, atherosclerosis, cancer, damage due to reperfusion (Kehrer J P. Free radicals as mediators of tissue injury and disease (1993) Crit Rev Toxicol 23:21-48). One of the ways a substance can interfere with these processes is through its action as an antioxidant or scavenger of free radicals.

Antioxidant effects: The first report on the antioxidant and anti-inflammatory properties of C-Phyco was done by Romay et al. (Romay C, et al. Antioxidant and anti-inflammatory properties of C-phycocyanin from blue-green algae (1998) Inflamm Res 47 (1):36-41), evaluating the potentials of C-Phyco as an antioxidant agent "in vitro" and "in vivo." C-Phyco was able to eliminate hydroxyl ($IC_{50}$=0.91 mg/ml) ($IC_{50}$: concentration of the additive that induces 50% of inhibition of the peroxidative damage) and alcoxyl radicals ($IC_{50}$=76 μg/ml) with a similar activity to 0.125 mg/ml of dimethylsulfoxide (DMSO) and 0.038 μg/ml of Trolox which are specific scavengers of these radicals, respectively. C-Phyco also inhibited the hepatic microsomal lipid peroxidation ($IC_{50}$=12 mg/ml) (Halliwell B. How to characterize a biological antioxidant. (1990) Free rad Res Comm; 9: 1-32). It is interesting to emphasize how the oxygen scavenging activity of C-Phyco was just 3 times smaller than that of superoxide dysmutase (SOD), the addition of SOD to C-Phyco did not alter its antioxidant ability, suggesting a different mechanism of action. Another indication of its antioxidant action is the ability to inhibit the damage of deoxyribose in a site-specific way. In the deoxyribose assay, the rate constant calculated for C-Phyco was similar to that obtained with the same method for some non-steroidal anti-inflammatory drugs such as indomethacine and the ibuprophene ($1.8 \times 10^{10}$ $M^{-1}S^{-1}$) (Parij N, et al. Linear and non linear competition plots in the deoxyribose assay for determination of rate constants for reaction of non steroidal anti-inflammatory drugs with hydroxyl radicals (1995). Free Rad Head; 23: 571-9).

This same group has recently reported that C-Phyco inhibits the 2,2'-azobis (2midinoprapane) dihidroxychloride (AAPH) erythrocyte haemolysis in a similar way to Trolox and ascorbic acid, very well-known antioxidants (Romay C, et al. Phycocyanin is an antioxidant protective of human erythrocytes against lysis by peroxyl radicals (2000) J Pharm Pharmacol 52: 367-368). Based on the values of $IC_{50}$, it was demonstrated that C-Phyco was 16 times more efficient antioxidant than Trolox and approximately 20 times more efficient than ascorbic acid. These findings were confirmed by another study (Hirata T, et al. Antioxidant activities of Phycocyanobilin prepared from Spirulina platensis (2000) J Appl Phycol 435-439) which demonstrated that the antioxidant activity of Phycocyanobilin (a component of the C-Phyco) was higher in molar quantities than alpha Tocoferol. The antioxidant effect of Phycocyanobilin was evaluated against the oxidation of methyl linoleate in a hydrophobic system or with phosphatidylcholine liposomes. The study also showed that C-Phyco from spray dried Spirulina had a similar antioxidant activity to C-Phyco from fresh Spirulina. These results suggest that the antioxidant activity of C-Phyco is attributable to Phycocyanobilin, the prosthetic group of C-Phyco, since the apoprotein component can be denatured during the drying process. The fact that the dried C-Phyco exhibits a similar activity level to the intact protein makes the C-Phyco preparation and use commercially feasible.

According to the results of Reddy et al (Reddy C M, et al. Selective inhibition of ciclooxygenase-2 by C-phycocyanin, a biliprotein from Spirulina platensis (2000) Biochem Biophys Res Commun 3: 599-603), C-Phyco from Spirulina platensis, is a selective cyclooxigenase-2 (COX-2) inhibitor with a very low $IC_{50}COX-2/IC_{50}COX-1$ (0.04) ratio. Interestingly, this study showed that the inhibition value $IC_{50}$ achieved by C-Phyco for COX-2 was much smaller (180 NM) than Celecoxib (255 NM) and Rofecoxib (401 NM), very well-known COX-2 selective inhibitors. The C-Phyco apoprotein component was responsible for the COX-2 inhibition since Phycocyanobilin and the reduced C-Phyco were ineffective. The authors suggest that the anti-arthritic, anti-inflammatory and hepatoprotective properties of C-Phyco reported in the literature are partially due to the COX-2 selective inhibition property although they do not exclude a similar effect of C-Phyco through its capacity to efficiently eliminate free radicals and to inhibit lipid peroxidation.

C-Phyco inhibits luminol amplified chemoluminescence (LCL) in a dose-dependent manner, probably through its capacity to eliminate free radicals (OH., $H_2O_2$, RO.) and peroxides increased during the respiratory burst of phagocytic cells. However, it is also possible that the C-Phyco could reduce the LCL level through other pathways, for example, impacting on the enzymes involved in the production of reactive oxygen species by activated phagocytes, NADPH oxidase and myeloperoxidase or interfering either with the linkage of the activator or with the arachidonic acid metabolic pathway. Recently, in an animal model of inflammation it was evidenced the inhibition of leukotriene B4 (LTB4) release by C-Phyco.

The inflammatory response induced by peroxide has been evaluated in a model "in-vitro" in order to identify agents with the potential scavenging effects of $H_2O_2$ and OH. Glucose oxidase (GO) injected in the paw of mice reacts with endogenous glucose and generates $H_2O_2$ with the successive production of OH radicals; both are responsible for the tissue damage and for the accompanying inflammatory changes (Spillert C R, et al. A peroxide-induced inflammation model for drug testing (1987) 21: 297-8). C-Phyco reduced glucose oxidase induced oedema in the mouse paw. This anti-inflammatory effect could be due, at least partially, to the elimination of hydroxyl radicals.

There is a frequent consensus in that the many in-vivo damages induced by $H_2O_2$ are due to its transformation into strongly reactive oxidants, mainly OH. (Halliwell B. How to characterize a biological antioxidant (1990) Free Rad Res Comm 9: 1-32) therefore, the OH scavenging action of C-Phyco is probably important for its anti-inflammatory effects.

Anti-inflammatory effects: C-Phyco is a phycobilin found in Spirulina (Sp) algae. Considering that this microalga is used as a nutritional supplement in many countries, including Cuba, it is conceivable that C-Phyco can also be used in diseases with an important inflammatory factor since there are reports concerning its anti-inflammatory activity (González R, et al. Anti-inflammatory activity of Phycocyanin extract in acetic acid-induced colitis in rats. (1999) Pharm Head 39; 1: 55-59). González et al evaluated the effect of an extract of C-Phyco in the acetic acid induced colitis, an animal model that mimics some of the acute inflammatory reactions observed in ulcerative colitis (Frettland D J, et al. Eicosanoids and inflammatory bowel disease: regulation and prospects for therapy (1990) Prost Leukotr Ess Fatty Acids; 41: 215-33). The most important finding in this study was that C-Phyco reduced the acetic acid induced colitis in rats, the first report of an anti-colitis effect of C-Phyco, which was assessed by its histological characteristics as well as through the structural analysis of the colon tissue and confirmed by myeloperoxidase (MPO) activity measurements. In this study, a significant reduction in neutrophil infiltration and in MPO activity in the damaged colon mucosa of the animals with colitis treated with C-Phyco was found, which supports its beneficial effect for this condition.

C-Phyco anti-inflammatory activity has also been found, with the same dose range, in the carrageen induced oedema in the rat paw and in the cotton speck granuloma in rats (Romay Ch, et al. Further studies on anti-inflammatory activity of phycocyanin in some animal models of inflammation (1998) Inflamm Head 47 (8):334-8). In these experimental models of inflammation as well as in experimental colitis, the metabolites of arachidonic acid play an important role. C-Phyco significantly reduced the arachidonic acid induced oedema of the ear in mice in a dose-dependent fashion, as well as the carrageen induced oedema of the rat paw. C-Phyco also showed anti-inflammatory activity in the cotton speck subchronic granuloma assay in which sterile specks of cotton are implanted in the rat armpit. The oral administration of C-Phyco resulted in a significant anti-inflammatory activity in every tested model. The anti-inflammatory activity observed was attributed to the oxygen scavenging and antioxidant activity of C-Phyco and may be due to its inhibitory effect on arachidonic acid metabolism.

Other reports have evaluated the role of C-Phyco in preventing chemically-induced liver damage derived from its referred antioxidant and anti-inflammatory effects. (Vadiraja B B, et al. Hepatoprotective effect of C-Phycocyanin: Protection for carbon tetrachloride and R-(+)-pulegone-mediated hepatotoxicity in rats (1998) Biochem and Biophys Res Com 249: 428-431). Vadiraja et al studied the effect of C-Phyco on the R-(+)-pulegone and CCl4 induced hepatotoxicity in rats. In this study a single dose (200 mg/kg) of C-Phyco administered intraperitoneally to rats, from 1 to 3 hours before the R-(+)-pulegone (250 mg/kg) or CCl4 (0.6 ml/kg) administration significantly reduced the hepatotoxicity produced by these chemical agents. It has been suggested that both agents cause hepatotoxicity through the generation of free radicals. Hepatoprotective effect: The hepatoprotective effect of C-Phyco was, therefore, adscribed to the inhibition of reactions involved in reactive metabolite generation and possibly to its radical removing activity. C-Phyco inhibits some of the reactions mediated by cytochrome P450, involved in the formation of reactive metabolites. In this case it is also possible that C-Phyco can act as an efficient radical remover. Recently, Bhat et al (Bhat V B, et al. C-phycocyanin: a potent peroxyl radical scavenger in vivo and in vitro (2000) Biochem Biophys Res Comun 1: 20-25) reported that C-Phyco inhibited, the lipid peroxidation induced by $CCl_4$ in rat liver "in vivo", this inhibition was concentration-dependent with an $IC_{50}$ of 11.35 µM. These studies have clearly demonstrated that C-Phyco is a potent peroxyl radical remover with a constant speed ratio of 1.54, compared to 3.5 for uric acid (a well-known peroxyl radical remover).

It is proposed that the decrease in the antioxidant defence mechanisms and the increase of the oxygen and nitrogen reactive species are causal factors in the decline of functions related with age and neurodegenerative diseases (Harman D. Aging: to theory based on free radical and radiation chemistry. (1956) J Gerontol 11: 289-300; Leibovitz B E, et al. Aspects of free radical reactions in biological systems: aging (1980) J Gerontol 35: 45-56; Ames B N, et al. Oxidants, antioxidants, and the degenerative diseases of aging (1993) Proc Natl Acad Sci USA 90: 7915-7922). Growing evidence suggests that the inflammatory processes are related to the oxidative damage of the central nervous system (SNC). The injection of the antioxidant enzyme superoxide dysmutase reduces the inflammation in some animal models. The antioxidants increase certain parameters of the immune function when they are added to isolated immune cells "in vitro" or when they are given as supplements to animals and human "in vivo" (Ian S N, et al. Antioxidant, cytokines, and influenza infection in aged mice and elderly humans (2000) J Infect Dis 182:S74-S80). A potential mechanism is the antioxidant effect on the immuno-regulatory molecule production such as cytokines. Cytokines are induced in response to brain damage and they can mediate and inhibit the cellular damage favouring restoration. Many clinical trials report the increased expression of cytokines in the cerebrospinal fluid (CSF) or in post-mortem cerebral tissue of patients that had a brain damage or infarct. Evidence indicates that pro-inflammatory cytokines such as IL-1 and TNF increase with the age (Lynch M A. Age-related impairment in long-term potentiation in hippocampus. A role for the cytokine, interleukin-1□? (1998) Prog Neurobiol 56: 571-589; Knoblach S M, et al. Early neuronal expression of tumor necrosis factor-□ after experimental brain injury contributes to neurological impairment. (1999) J Neuroimmunol 95: 115-125). C-Phyco has the highest antioxidant activity of all compounds found in the Sp, as evaluated against the oxidation of methyl linolate in a hydrophobic system (Hirata T, et al. Antioxidant activities of phycocyanobilin prepared from spirulina platensis (2000) J Appl Phycol 12: 435-439).

In one study (Gemma C, et al. Diets enriched in foods with high antioxidant activity to be reviewed age-induced decreases in cerebellar □-adenergic function and increases in pro-inflammatory cytokines. (2002) J Neurosci 22; 14: 6114-6122) 344 aged Fischer rats fed during 14 days with a diet based only on Sp, showed an improvement of the b-adrenergic receptor function, a reduction of the pro-inflammatory cytokines (evidenced by the decrease of the levels of mRNA of TNF-□ and TNF-□) and the reduction of malonyldialdehyde levels (MDA), a marker of oxidative damage, in the cerebellum. These events did not take place in rats fed diets supplemented with equivalent amounts of cucumbers or food with low levels of ORAC (oxygen reactive absorption capacity).

Neuroprotective effect: A recent, sophisticated and interesting study shows that the oral administration of C-Phyco (100 mg/kg) in rats prevents glial reactivity and the behaviour induced by kainic acid in the rat hippocampus, suggesting a protective effect on neurons. The study showed that C-Phyco reduced the experimental epileptic condition, suggesting a possible therapeutic participation in the treatment of certain types of epilepsy. According to these authors (Rimbau V, et al. Protective effect of C-phycocyanin against kainic acid-induced neuronal damage in rat hippocampus (1999). Neuroscience Letters; 276: 75-78), kainic acid causes excytotoxicities that generate the production of oxygen reactive species. Therefore, they postulate that the protective effect of C-Phyco in the neuronal damage could be due to the elimination of free radicals and their antioxidant properties. An interesting feature in this study is the finding that the oral administration of C-Phyco exerts an effect on the hippocampus, crossing the blood brain barrier. These findings and the virtual lack of toxicity of C-Phyco suggest that this photochemical could be used in the treatment of neurodegenerative disease such as, Alzheimer disease and Parkinson, which are characterized by neuronal damage induced by oxidative stress.

Antiallergic effects: besides the anti-inflammatory properties of C-Phyco mediated by its antioxidant properties already referred to in detail, it has been reported that C-Phyco has anti-inflammatory effects on the induced allergic inflammatory response and on the histamine release of isolated rat mast cells (Remirez D, et al. Role of histamine in the inhibitory effects of phycocyanin in experimental models of allergic inflammatory response (2002) Mediators of Inflammation, 11: 81-85). In experiments "in vivo", C-Phyco was administered 1 hour before the challenge with ovoalbumin (Ova) in the ear of previously Ova sensitized mice. One hour later, the MPO activity and the oedema was evaluated in the ear. C-Phyco, significantly reduced both parameters and inhibited the release of histamine of the isolated rat peritoneal mast cells. The effect of C-Phyco was dose-dependent.

The increased vascular permeability to plasma proteins is one of the characteristics of the allergic inflammatory reaction where mast cells play an important role because they can secrete preformed vasoactive mediators, mainly histamine and serotonin, in rats and mice (Halpern B N, et al. On the nature of the chemical mediators involved in anaphylactic reaction in mice. (1963) Br J Pharmacol 20: 389-398; Ohuchi K, et al. Pharmacological analysis of the vascular permeability response in the anaphylactic phase of allergic inflammation in rats (1985) Eur J Pharmacol 117: 337-345). It been has demonstrated that mast cells also contain pre-formed cytokines, such as TNF-□ and vascular permeability factor/vascular endothelial cell growth factor, among others, which can be secreted in IgE-dependent reactions and can produce mast cell effector and immunoregulatory abilities during the allergic inflammatory reaction. In this reaction the participation of newly synthesized lipid mediators from mast cells, such as prostaglandin D2, leukotrienes (LTC4, LTD4, LTE4, LTB4) and the platelet activating factor (PAF), and reactive oxygen species (ROS), are also important (Williams C M, et al. The diverse potential effector and immunoregulatory roles of mast cells in allergic diseases. (2000) J Allergy Clin Immunol 105: 847-859; Fantozzi R, et al. Mast cell and neutrophil interactions: a role for superoxide anion and histamine. (1985) Agents Actions 16: 260-264). C-Phyco reduces prostaglandin D2 levels and LTB4 in the arachidonic acid induced inflammation assay in mouse ears (Romay C, et al. Effects of phycocyanin extract on prostaglandin E2 levels in Mouse ears inflammation test. (2000) Arzneim Forsch/Drug Head 50: 1106-1109; Romay C, et al. Phycocyanin extract reduces leukotrienes B4 levels in arachidonic acid-induced mouse ear inflammation test (1999) J Phar Pharmacol 51: 641-642).

The inhibitory effect of C-Phyco on the isolated rat mast cell histamine release supports the contribution of this event in the mechanism of action of C-Phyco as an anti-inflammatory agent.

There is evidence that ROS, such as superoxide anions, hydrogen peroxide, and peroxyl hydroxyl radicals, can start the arachidonic acid cascade, PAF synthesis or histamine release. It has been demonstrated that ROS degranulate mast cells allowing the release of histamine, serotonin, TNF-□ and other inflammation mediators. C-Phyco is able to purge peroxide, hydroxyl and alcoxyl radicals (Lissi E A, et al. Kinetics of phycocyanin bilin groups destruction by peroxyl radicals. (2000) Free Radic Biol Med 28: 1051-1055)

Besides the antioxidant, anti-inflammatory and anti-allergic properties demonstrated for C-Phyco, antitumor properties have also been observed.

Anticancer effects: Schwartz et al (Schwartz J, et al. Regression of experimental hamster cancer by beta carotene and algae extracts. (1987) Oral J Maxillofac Surg; 45: 510-515) studied the effect of the administration of 250 µg of a Spirulina extract in a squamous oral carcinoma induced by DMBA (7,12-dimethylbenz(a)-anthracine), other treatments included the injection of beta-carotenes, canthaxanthin and 13 cis-retinoic acid. All the treatments were applied twice a week during 4 weeks. At the end of the treatment, there was a total regression of the tumor in 30% of the animals treated with the extract, 20% in those treated with beta carotenes and 15% in those treated with canthaxanthin. There were partial tumor regressions in the remaining 70% of the animals treated with the extract. An interesting observation in this study was that the extract of the alga was more effective than beta carotene alone, suggesting a synergic effect along with several components of the alga. In another study of this same group (Schwartz J, et al. Algae-derived phycocyanin is both cytostatic and cytotoxic to oral squamous cell carcinoma (human or hamster) (1987). J Dent Head 66: 160) they demonstrated that C-Phyco derived from the alga, had cytostatic and cytotoxic abilities against squamous cell carcinoma (in human and hamster).

In a study (Liu A N D, et al. Inhibitory effect of phycocyanin from Spirulina platensis on the growth of human leukemia K562 cells (2000) J Appl Phycol 12: 125-130), C-Phyco from Spirulina platensis inhibited the growth of the human leukemia K562 cell line. The effect of C-Phyco was initially studied following the growth of the K562 cells in semi-solid agar cultures at concentrations of 20, 40, 80 and 169 $mg^{-1}$. The results showed that C-Phyco inhibited the growth of the K562 leukemia cells in a dose-dependent way with statistically significant inhibition observed at 80 and 160 $mg^{-1}$. The effect of C-Phyco was also studied using the cell viability in the reduction dye XTT assay. Once again C-Phyco, inhibited the cellular viability in a dose-dependent way. The $IC_{50}$ value of C-Phyco was of 72.5 mg-1. Flow cytometry experiments, based on the analysis of the DNA content revealed that the accumulation of K562 cells occurs in the G-1 phase when the cells were incubated with C-Phyco for 6 days. The highest percentage of cells in the G-1 phase was at the 40 and 80 mg-1 concentrations of C-Phyco. The DNA fragmentation analysis did not show the typical apoptosis stepping pattern, indicating that a different mechanism can be involved in this inhibition.

Previous studies report the selective inhibition of COX-2 by C-Fico (Reddy C M, et al. Selective inhibition of cicloxygenase-2 by C-phycocyanin, a biliprotein from Spirulina platensis (2000) Biochem Biophys Res Commun 3: 599-603), in this study and based on this property the group (Bobbili V. V, et al. Phycocyanin-mediated apoptosis in AK-5 tumor cells involves down-regulation of Bcl-2 and generation of ROS. (2003) Mol Cancer Therapy 2: 1165-1170) studied the effect of C-Phyco on a hystiocytic rat tumoral cell line. Diverging from the results of a previous study, where apoptosis did not mediated anti-tumor effects, C-Phyco induced programmed apoptotic death of AK-5 cells; this program involves the caspase-3 activation. The apoptotic death mediated by C-Phyco is induced through the generation of ROS. Bcl-2, an apoptosis inhibitor, regulated the ROS generation. AK-5 cells transfected with the Bcl-2 gene became resistant to the death induced by C-Phyco. The over-expression of Bcl-2, inhibited the ROS production in AK-5 cells treated with C-Phyco, which demonstrates that apoptosis induced by C-Phyco in AK-5 cells is inhibited by Bcl-2 through the regulation of free radical generation. C-Phyco, as well as other inhibitors of COX-2 could be used as a possible chemotherapeutic agent for its apoptotic activity on tumor cells.

The most recent study on the anti-cancer properties of C-Phyco, was reported by Subhashini et al. (Jagu Subhashini, et al. Molecular mechanisms in C-Phycocyanin induced apoptosis in human chronic myeloid leukemia cell line-K562. (2004) Biochem Pharmac 68: 453-462) who evaluated the effect of a highly purified C-Phyco on the growth and multiplication of the human chronic myeloid leukaemia cell line K562. The results indicate a significant decrease (49%) in the proliferation of the K562 cells treated with 50 µM of C-Phyco in 48 hours. Also, electron microscopy and fluorescence studies revealed apoptotic characteristics such as cellular retraction, membrane protrusions and nuclear condensation. Genomic DNA electrophoresis of cells treated with C-Phyco showed the typical pattern of fragmentation of the apoptotic cells. Flow cytometry analysis of apoptotic cells with 25 and 50 µM of C-Phyco during 48 hours showed 14.11 and 20.93% of cells in sub G0/G1 phase respectively. The treatment with C-Phyco of the K562 cells also resulted in cytochrome C release on the cytosol and rupture of poly (ADP) ribose polymerase (PARP). This study also showed a decrease of anti-apoptotic Bcl-2 but without any change in proapoptotic Bax, therefore the Bcl-2/Bax ratio favours apoptosis. The effects of C-Phyco seem to be mediated by the entrance of C-Phyco into the cytosol through an unknown mechanism. The present studies also demonstrate that C-Phyco induces apoptosis in K562 through cytochrome C released from the mitochondria to the cytosol, the rupture of PARP and the decrease of Bcl-2.

According to a Japanese patent (Dainippon Ink & Chemicals, Inc. (DIC). Anti-tumoral agents containing phycobillin. (1983) Japanese Patent Not. 58-65216) the oral administration of C-Phyco increased the survival of mice injected with tumor cells from the liver. The lymphocytic activity in the treated group was significantly higher than the control group, suggesting a certain degree of stimulation of the immune system.

Other properties of C-Phyco demonstrated in different studies: Cheng-Wu et al (Cheng-wu Z, et al. The effects of polysaccharide and phycocyanin from Spirulina platensis on peripheral blood and hematopoietic system of bone marrow in mice. (1994). Book of Abstracts. Second Asia Pacific Conference on Algal Biotechnology; 58) in a preliminary study on the effect of polysaccharides and the C-Phyco in mice peripheral blood and bone marrow of the haematopoietic system demonstrated that C-Phyco had a high erythropoietin (EPO)-like activity.

DESCRIPTION OF THE INVENTION

The present invention describes the use of a bio-regulator pharmaceutical compound addressing the promotion, release or recovery of the affected capacities of the individual in order to achieve the restoration of the homeostatic functional imbalance that has been altered with the disease.

The compound is original in its formulation since it is formed by a protein belonging to the interferon family that is combined with a product of natural origin, having demonstrated, in our invention, its effectiveness in the treatment of autoimmune and allergic diseases, and in cancer.

The compound referred to in this invention is composed of alpha interferon (IFN-α), specifically recombinant IFNα-2b and C-Phycocyanin, which can be included in a pharmaceutical combination for parenteral or oral administration with an appropriate excipient.

The above mentioned pharmaceutical combination can be used as a treatment method through the separate administration of the active components in the same individual for a single treatment.

In a particular study in the experimental autoimmune encephalitis (EAE) model, the components of the combination were administered through different routes; IFN-α was given intra-peritoneally and C-phycocyanin was offered orally as part of the same treatment. The separate administration of the components through different routes and their administration as a part of a pharmaceutical preparation through a single route using the same dosages showed no significant differences. This demonstrated that the administration route has no effect and the combination can be also administered through the intramuscular, intravenous, subcutaneous, oral, nasal and intrathecal routes.

The originality of the invention is the demonstration of the effect of the IFN-α/C-Phyco pharmaceutical preparation and their separate active principles in the induction of adaptive and natural regulatory T cells.

This important property of the immune system had already been suggested for IFN-α, but in our invention, besides demonstrating it for IFN-α, we report for the first time the induction of regulatory T cells by C-Phycocyanin, demonstrating a synergic effect of both components in the IFN-α/C-Phyco pharmaceutical compound. This supports its use in diseases producing a decrease in the number or function of regulatory T cells (rTc), such as allergic and autoimmune diseases where the development of a crisis is prevented, especially in the relapsing forms of these diseases.

Hence, through the present invention we were able to simultaneously restore the effector-regulator balance that is disrupted in allergic and autoimmune diseases due to a loss in immuno-regulation, while intervening at the same time, in different stages of the pathogenesis of these diseases, where the anti-inflammatory immunomodulatory and antioxidant properties, described in the literature for IFN-α and C-Phycocyanin, are potentiated by the combination of both active principles.

On the other hand, this invention demonstrates the synergic effect of the pharmaceutical IFN-α/C-Phyco preparation as compared to the activity of the independent components, in relation to their anti-proliferative, anti-oxidant and anti-inflammatory properties and in their induction capacity of tumor cell apoptosis.

The novelty of the invention, in this case, is that the pharmaceutical compound was shown to have significantly higher anti-cancer effects than the independent components regarding their anti-proliferative and apoptosis inducing properties in tumor cells. This is evidenced by the positive regulation of the p53 proteins and later p21, required to maintain the arrest of the cellular cycle in the G2/M phase and the apoptosis following the DNA damage.

Additionally, a statistically significant synergic anti-proliferative and dose-dependent effect of the IFN-α/C-Phyco compound was shown for growth inhibition of tumor lines of different origins.

One of the most widely studied effects of the C-Phyco is its antioxidant capacity in in-vitro and in-vivo tests (Romay C, et al. Antioxidant and anti-inflammatory properties of C-Phycocyanin from blue-green algae (1998) Inflamm Head 47 (1):36-41). C-Phyco was able to eliminate hydroxyl and alcoxyl radicals with same scavenger activity as others used specifically for these radicals. C-Phyco also inhibited hepatic microsomal lipid peroxidation (Halliwell B. How to characterize a biological antioxidant. (1990) Free rad Head Comm; 9: 1-32). The anti-inflammatory, immunomodulatory and antiproliferative effects and apoptosis inducing ability in tumor cells of C-Phyco is considered to be mainly mediated by its potent antioxidant activity. This can explain the anti-cancer effect of C-Phyco, since most neoplastic processes have a chronic inflammatory component and other elements that express a marked oxidative stress.

These are crucial aspects for understanding how the regulation of the cellular cycle and the apoptotic machinery are important in the growth and development of neoplasm. These signaling points give place to the activation of pathways that lead to programmed cell death if cell damage is not repaired (Pietenpol J A, Stewart Z A. Cell cycle checkpoint signaling: cell cycle arrest versus apoptosis. (2002) Toxicology 181-182: 475-481.

The anti-proliferative and apoptosis inducing effects of IFN-α on tumor cells are very well known. They produce a lengthening of phase G1, a reduction in the speed of entry to phase S and slow down phase S and G2 (Balkwill F, et al. Interferon affects both G1 and S+G2 in cells stimulated from quiescence to growth. (1978) Nature 274: 798-800). The cumulative effect of the lengthening of the cellular cycle by IFN-α, in normal cells as well as tumor cells leads to cytostasis, an increase in cell size and apoptosis (Otsuki T, et al. Human myeloma cell apoptosis induced by interferon-α. (1998) BR J HAEMATOL 103: 518-529).

Tumor cells develop alterations in one or more proteins that control the progression of the cell cycle, among them proto-oncogenes such as the bcl2 regulated by IFN can be found (Koshiji M, et al. Apoptosis of colorectal adenocarcinoma (COLO201) by tumor necrosis factor-alpha and/or interferon-gamma resulting from down-regulation of Bcl-2 expression. (1998) Clin Exp Immunol 111: 211-218). In a particular example of our invention a synergic and dose dependent effect was demonstrated in the negative regulation of bcl2 on tumor cells when stimulated by the IFN-α/C-Phyco combination.

One of the pathways for apoptosis induction involves the binding of Fas to FasL, which results in the recruitment of the protein containing a FADD death domain and the consequent activation of caspases, such as caspase-8. IFN-α positively regulates the expression of Fas and can therefore operate through the apoptotic pathway mediated by Fas as demonstrated in another particular example of our invention where it was also shown that the IFN-α/C-Phyco pharmaceutical compound produced a positive and significant modulation of the expression of Fas in tumor cells.

COX-2 is a well-known anti-apoptotic molecule and it has been reported that C-Phyco is a selective inhibitor of COX-2, thus favoring the programmed cell death of tumor cells (Reddy C M, et al. Selective inhibition of ciclooxygenase-2 by C-Phycocyanin, to biliprotein from Spirulina platensis (2000) Biochem Biophys Head Commun 3: 599-603). In our invention we also demonstrate that the IFN-α/C-Phyco compound significantly diminishes the levels of expression of COX-2 and in a dose dependent manner, making this a possible mechanism that may explain the apoptosis induction effect on tumor cells for the described combination.

A study carried out by Subhashini et al. (Jagu Subhashini, et al. Molecular mechanisms in C-Phycocyanin induced apoptosis in human chronic myeloid leukemia cell line-K562. (2004) Biochem Pharmac 68: 453-462) showed that C-Phyco induces apoptosis in the K562 cell line by the release of cytochrome-C from the mitochondria to the cytosol and the decrease in bcl-2. In our invention we show that the above mentioned pharmaceutical compound has a positive synergic effect as compared to its separate components in the level of induction of the cytochrome-C expression, thus regarding this as a mechanism for the induction of apoptosis of tumor cells produced by this compound.

In clinical practice it has been demonstrated that the combination of IFN-α with hormones, chemotherapy and/or IL-2 could increase the patient's response and prolong survival to many types of tumors, however, their integration in a therapeutic method has been limited by their respective toxicities. We therefore propose the use of the pharmaceutical compound described in our invention since, besides producing a synergic effect of both components in its anti-proliferative, cytotoxic and antioxidant effect and in inducing apoptosis in tumor cells, thereby justifying clinical results, there is a large amount of evidence on the innocuousness and lack of toxicity of C-Phyco.

DESCRIPTION OF THE FIGURES

FIG. 8: Effect of the IFN-α/C-Phyco combination and the separate active principles on the expression of the gene Fas in the cellular line K562.

EXAMPLES

Example 1

Figure 1A:
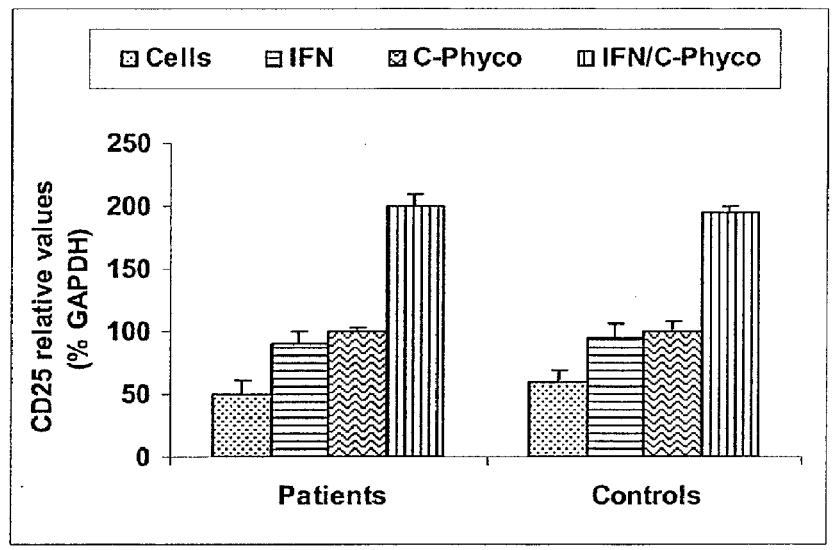
FIG. 1: Effect of the separate treatments and the IFN-α/C-Phyco combination on the expression of marker genes of natural regulatory T cells (A and B) and adaptive regulatory T cells (C and D) by RT-PCR in patients with Multiple Sclerosis (MS).
Figure 1B:
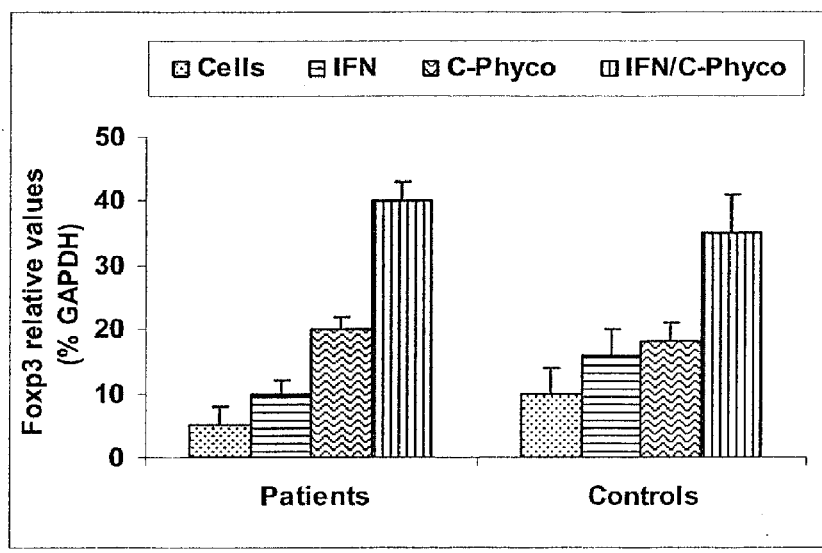
Figure 1C:
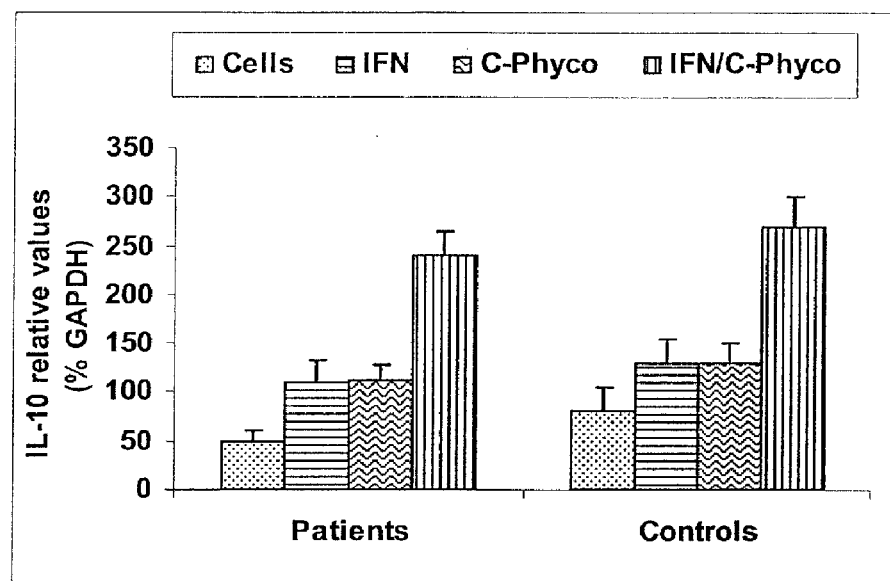
Figure 1D:
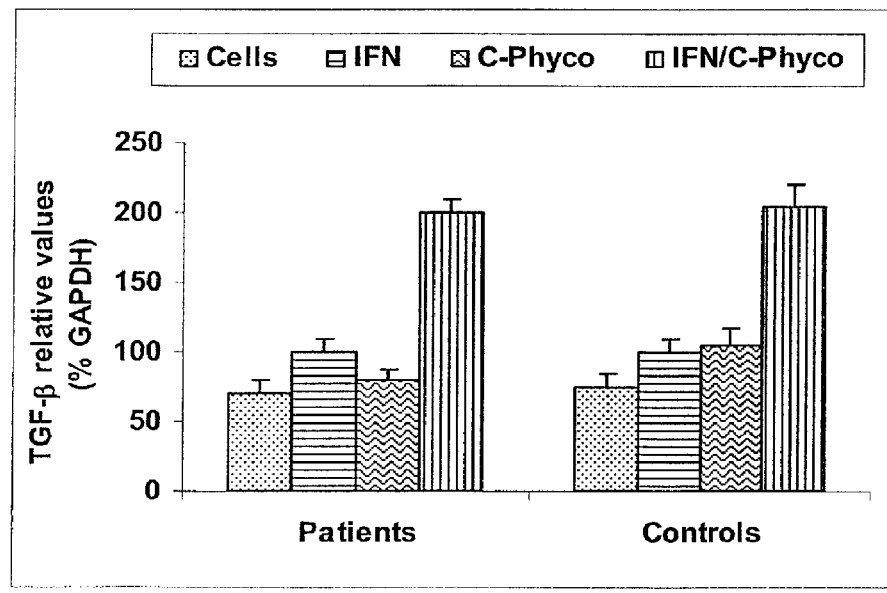

Therapeutic Effect of the IFN-α/C-Phyco Combination and its Separate Active Principles in a Model of EAE The IFN-α/C-Phyco combination was tested in a biomodel of EAE to evaluate its therapeutic effect:

Female Lewis rats with an average live weight of 130 g were immunized, subcutaneously with 5 mg of guinea pig spinal cord homogenate in PBS (50%) and Freund's complete adjuvant (50%) on days 0 and 6. The therapeutic schedule was started ten days after the first immunization by using, through the intraperitoneal route, the IFN-α/C-Phyco combination (200 ng/kg/day-740 ng/kg/day), the separate active principles IFN-α (200 ng/kg/day) and C-Phyco (200 ng/kg/day), and a placebo (PBS). It was monitored for 10 days through the evaluation of the clinical evolution of the disease according to the following clinical index: 0; no alterations, 1; complete tail paralysis, 2; paralysis of one of the hind limbs, 3; the complete paralysis of the hindquarters, 4; the complete paralysis of the hindquarters and the paralysis of the forequarters, 5; death. The weight loss and vesical or rectal sphincter incontinence are also clinical signs of the disease in the animal and were evaluated by adding 0.5 to the clinical index mentioned above. Forty days after the first immunization the animals were anesthetized and slaughtered, the encephalon and the spinal cord of each animal was processed (fixation in 10 formalin %, H&E and Luxol Blue stained) for histopathological analysis. The histopathological criteria considered were, number and size of the perivascular inflammatory infiltrate, demyelinating lesions, neuron or glial apoptosis and astrocytic reactivity. All observations were carried out blindly.

As shown in Table 1 the IFN-α/C-Phyco combination protects the experimental animals induced to develop EAE, since only 50% of these animals developed the weakest form of the disease and the rest did not get sick. This was not so in the rest of the groups where the incidence of the disease was of 100% (groups treated with the separate active principles and the placebo). The mean of the clinical index of the group treated with the IFN-α/C-Phyco combination is of 0.37±0.47, that of the groups treated with the separate active principles is 1.37±1.7 for IFN-α and 1.5±1.6 for C-Phyco and that of the group treated with the placebo is 1.7±1.4. Eight rats were used per group and the comparisons were carried out according to the multiple comparison test of Newman Keuls with $p<0.001$.

TABLE 1

Clinical-therapeutic effect of the IFN-α/C-Phyco combination and their separate active principles in rats induced to develop EAE.

| Groups | Incidence (%) | Initial Day (Mean ± SE) | Clinical index (Mean ± SE) | Maximum | Minimum | Days sick |
|---|---|---|---|---|---|---|
| Control | 0 | 0 | 0 | 0 | 0 | 0 |
| IFN-α | 100 | 12.5 ± 0.57 | 1.37 ± 1.7 | 5 | 1 | 12.7 ± 4.1 |
| C-Phyco | 100 | 13.7 ± 2.3 | 1.5 ± 1.6 | 4 | 0.5 | 15.5 ± 6.7 |
| IFN-α/C-Phyco | 50 | 12 ± 0 | 0.37 ± 0.47 | 1 | 0 | 9 ± 1.4 |
| Placebo | 100 | 12.2 ± 0.5 | 1.7 ± 1.4 | 4 | 0.5 | 13.2 ± 8.1 |

As observed in Table 2, the results of the pathologic anatomy study of the encephalon and spinal cord of the animals from different groups demonstrate that although the astrocytic reactivity is the same, the number and size of the perivascular inflammatory infiltrate is smaller in the group treated therapeutically with the pharmaceutical compound than in that receiving the placebo ($p=0.028$ Independent Samples T Test).

TABLE 2

Effect of the IFN-α/C-Phyco combination and their separate active principles on the perivascular inflammatory infiltrate in the brain and spinal cord of rats induced to develop EAE.

| Groups | Number perivascular inflammatory infiltrates (mean ± SE) |
|---|---|
| Control | 0 |
| IFN-α | 4.5 ± 1.9 |
| C-Phyco | 2.25 ± 1.25 |
| IFN-α/C-Phyco | 2 ± 0.8 |
| Placebo | 5 ± 2.1 |

This experiment demonstrates that the IFN-α/C-Phyco combination protects the animals from developing the disease in its more severe clinical form.

Example 2

The Therapeutic Effect of the IFN-α/C-Phyco Combination Using Different Administration Routes To evaluate the effect of the IFN-α/C-Phyco combination using different administration routes for the components, female Lewis rats, with an average body weight of 130 g, were immunized subcutaneously with 5 mg of guinea pig spinal cord homogenate in PBS (50%) and Freund's complete adjuvant (50%), on days 0 and 6. The therapeutic schedule was started ten days after the first immunization, as follows: group I: IFN-α/C-Phyco combination (200 ng/kg/day-7400 μg/kg/day) administered intraperitoneally, group II: IFN-α/C-Phyco combination where the IFN-α is administered intraperitoneally (200 ng/kg/day) and the C-Phyco orally (7400 μg/kg/day) through gastric intubation and group III: placebo. This therapeutic schedule was followed for 10 days. Clinical evaluations were carried out as explained in the previous example.

Results are shown in Table 3. The IFN-α/C-Phyco combination either intraperitoneally or by the intraperitoneal/oral routes respectively, protects the experimental animals induced to develop EAE. In both cases only 40% of the animals developed the disease compared to the placebo group where the 100% of the animals were sick. The mean clinical index of the group treated intraperitoneally with the IFN-α/C-Phyco combination was 0.37±0.17, and that for the group treated orally with the IFN-α/C-Phyco combination was 0.35±0.11 and for the placebo group it was 1.7±1.4. Eight rats per group were used. The comparison between the groups was statistically significant $p<0.001$. The multiple comparison test of Newman Keuls was used.

TABLE 3

The clinical-therapeutic effect of the IFN-α/C-Phyco combination for the different administration routes in rats induced to develop EAE.

| Groups | Incidence (%) | Initial day (Mean ± SE) | Clinical index Mean ± SE | Maximum | Minimum | Days sick |
|---|---|---|---|---|---|---|
| IFN-α/C-Phyco intraperitoneal | 52 | 12.1 ± 1.2 | 0.3 ± 0.25 | 1 | 0 | 9 ± 1.6 |
| IFN-α/C-Phyco Intraperitoneal/oral | 50 | 12 ± 1.1 | 0.37 ± 0.47 | 1 | 0 | 9 ± 1.4 |
| Placebo | 100 | 12.2 ± 0.5 | 1.7 ± 1.4 | 4 | 0.5 | 13.2 ± 8.1 |

Example 3

Evaluation of the Induction of Natural and Adaptive rTc Effect for the IFN-α/C-Phyco Combination and its Separate Active Principles in Mononuclear Cells of MS Patients In order to evaluate the induction of rTc effect of the IFN-α/C-Phyco combination, as well as its separate active principles in MS patients, 20 ml of peripheral blood was extracted from 10 patients with relapsing-remitting MS (RRMS) clinically defined by Nuclear Magnetic Resonance (NMR) and 10 controls (apparently healthy individuals), the mononuclear cells were isolated by the Ficoll gradient (Serotec-Biochem, Berlin, Germany) and they were divided into 4 experimental groups of $3\times10^6$ Cells/group in RPMI 1640 media, the groups were treated as follows: A) Cells alone, B) Cells+5 µM IFN-a2b, C) Cells+20 µM C-Phyco, D) Cells+5 µM IFN-a2b/20 µM C-Phyco for 4 hours at 37 degrees Celsius and 5% CO2. Afterwards, the cells were washed and a total RNA extraction was made by the Tri-reagent method (Chomczynski P. TO reagent for the sail-step simultaneous isolation of RNA, DNA and proteins from cell and tissue samples. (1993) BioTechniques, 15, 532-537). The the Reverse Transcription-Polymerase Chain Reaction (RT-PCR) (Kit RT-PCR core Perkin Elmer) was carried out using 1 µg of total RNA/experimental group. The RT reaction was carried out in a total volume of 20 µl that was then divided into 2 PCR reactions of 10 µl each. Primers of the reaction were used for the amplification of markers of natural and adaptive rTc. The oligonucleotids used were designed using the sequences of the database of the National Center for Biotechnology Information (NCBI) as the reference; they are explained below:

CD25: Oligo 5'-sequence of 20 base pairs (bp) from position 618 to 637. Oligo 3'-sequence of 20 bp from position 1053 to 1072, they amplify a band of 454 bp of the sequence with access number NM_000417.

Foxp3: Oligo 5'-sequence of 20 bp from position 482 to 501. Oligo 3'-sequence of 20 bp from position 762 to 781, they amplify a band of 299 bp of the sequence with access number NM_014009.

IL-10: Oligo 5'-sequence of 20 bp from position 358 to 377. Oligo 3'-sequence of 22 bp from position 687 to 709, they amplify a band of 351 bp of the sequence with access number NM_000572.

TGF-β: Oligo 5'-sequence of 19 bp from position 1209 to 1227. Oligo 3'-sequence of 19 bp from position 1564 to 1582, they amplify a band of 373 bp of the sequence with access number NM_000660.

GAPDH: Oligo 5'-sequence of 18 bp from position 386 to 403. Oligo 3'-sequence of 20 bp from position 561 to 580, they amplify a band of 164 bp of the sequence with access number NM_002046.

GAPDH was used as a gene of constitutive expression to normalize the relative values obtained with the Molecular Analysis software from the densitometry of agarose gels 2% where the PCR products were run.

The results are expressed as the mean or median (according to the distribution of the variable) of the relative values of RNA normalized with GAPDH; the means or medians were compared of the 3 experimental groups treated compared to the control group with cells alone and the corresponding statistic p value was calculated in the patients and controls. As shown in FIGS. 1A, B, C and D, there is a rTc induction effect that is expressed by an increase of their markers that is found when cells are treated with the separate active principles and with the combination, demonstrating a statistically significant difference with a value of p=0.023 (paired t test) for CD25 (A), p=0.037 (paired t test) for Foxp3 (B), p=0.015 (paired t test) for IL-10 (C) and p=0.025 (Wilcoxon) for TGF-β (D) after the treatment with the IFN-α/C-Phyco combination. This shows that there is a synergic effect of the IFN-α/C-Phyco combination for rTc induction both in the patients and controls.

Figure 2:
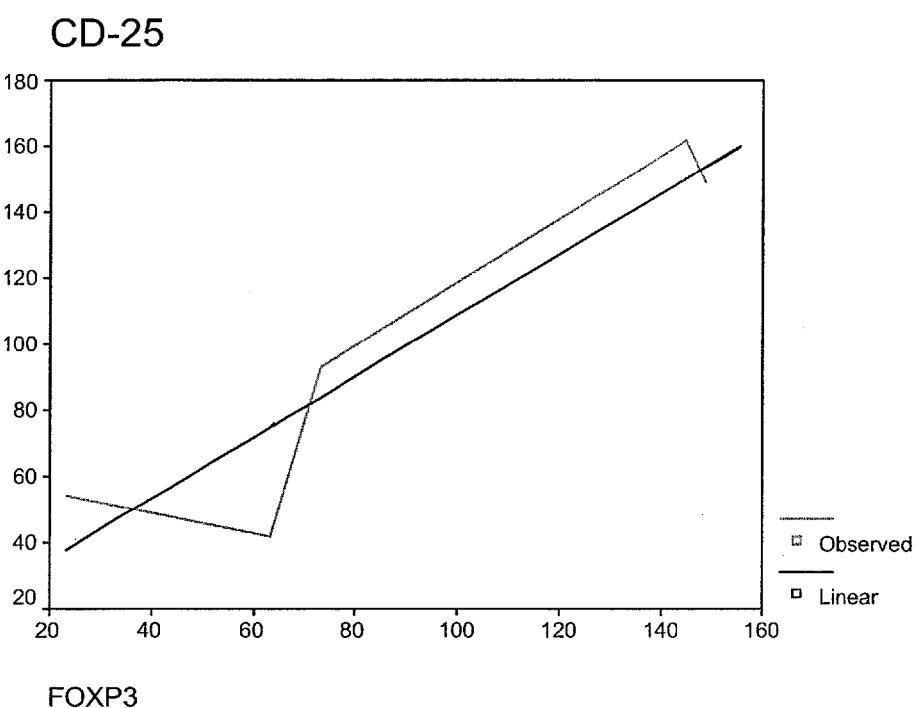
FIG. 2: Effect of the IFN-α/C-Phyco combination on the relationship of CD25/Foxp3 in patients with Multiple Sclerosis.
Figure 3A:
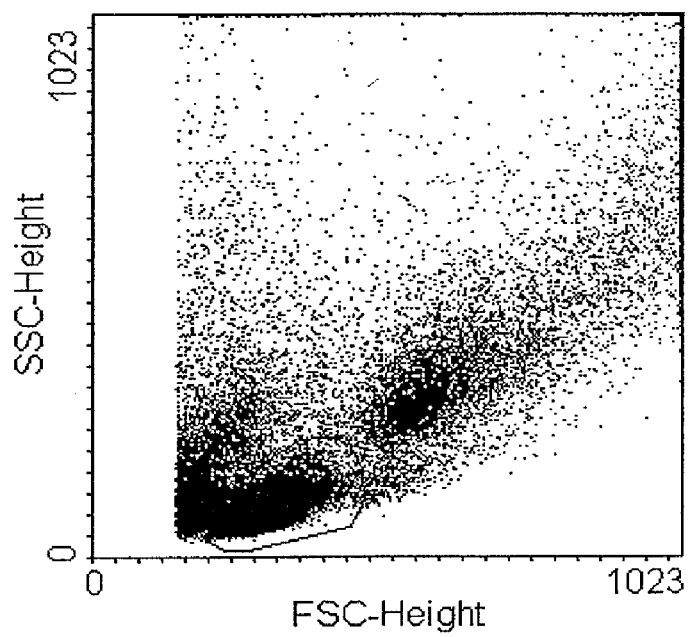
FIG. 3: A-P) Flow cytometry of the expression of CD4+ CD25+ in mononuclear cells from peripheral blood treated with the separate active principles and with the IFN-α/C-Phyco combination Q-R) Induction effect of CD4+CD25+ and CD4+CD25$^{high}$ cells of the separate active principles and of the IFN-α/C-Phyco combination.
Figure 3B:
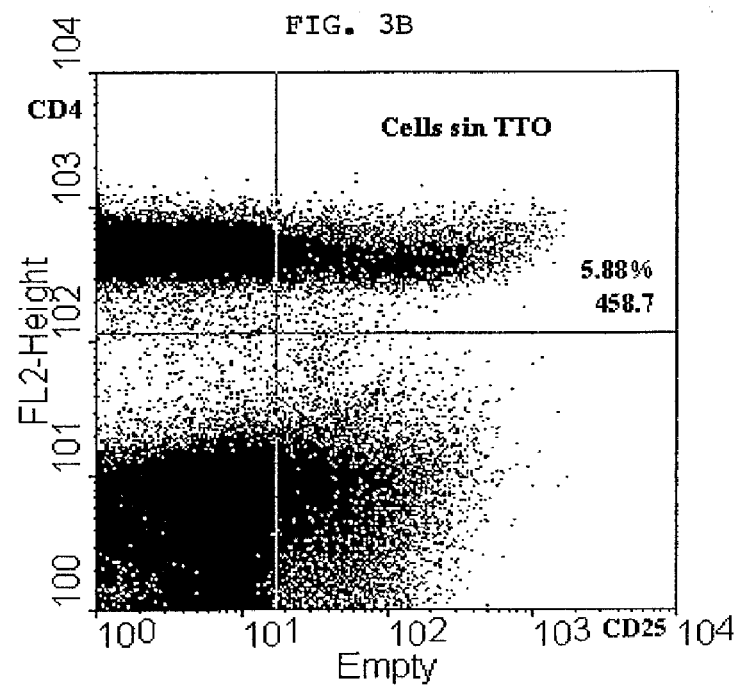
Figure 3C:
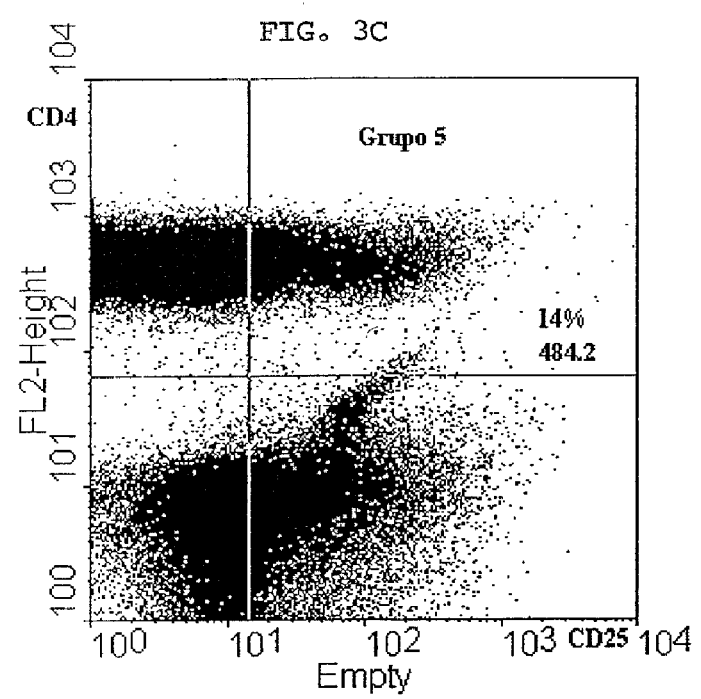
Figure 3D:
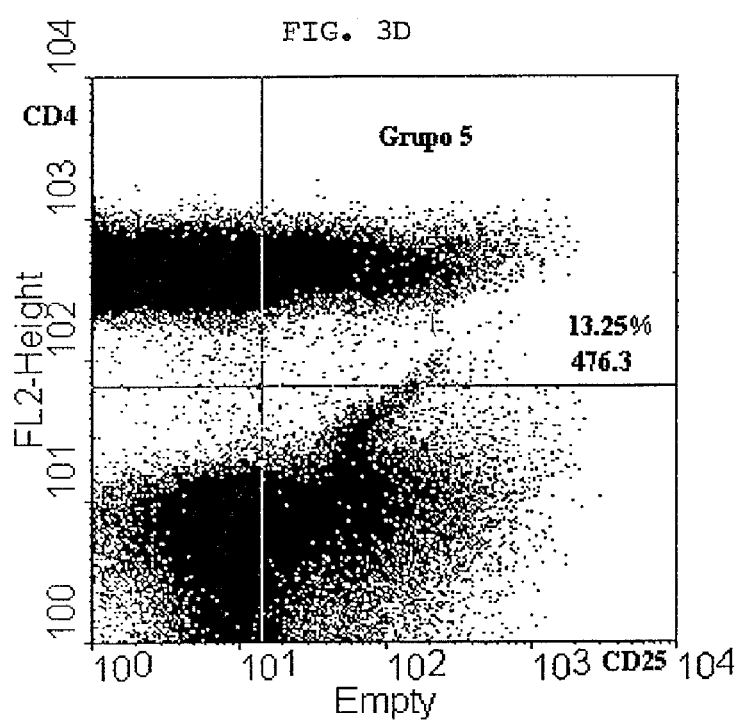
Figure 3E:
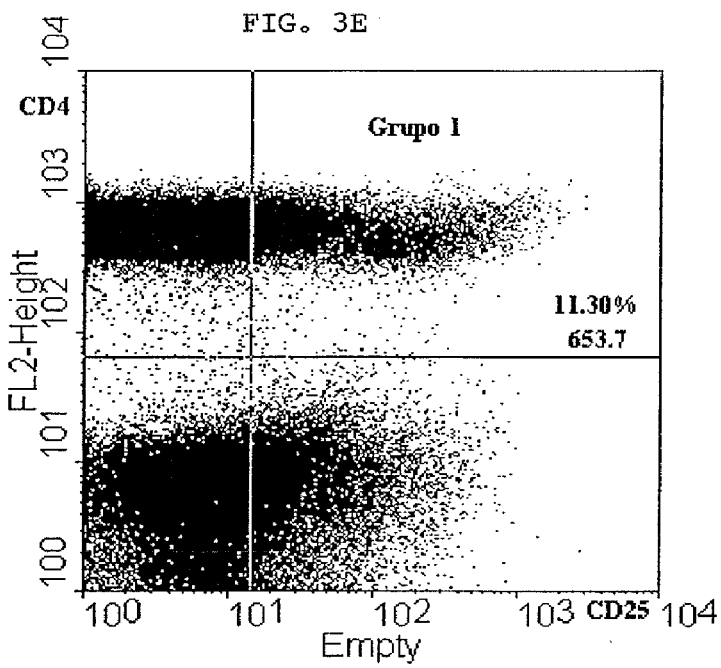
Figure 3F:
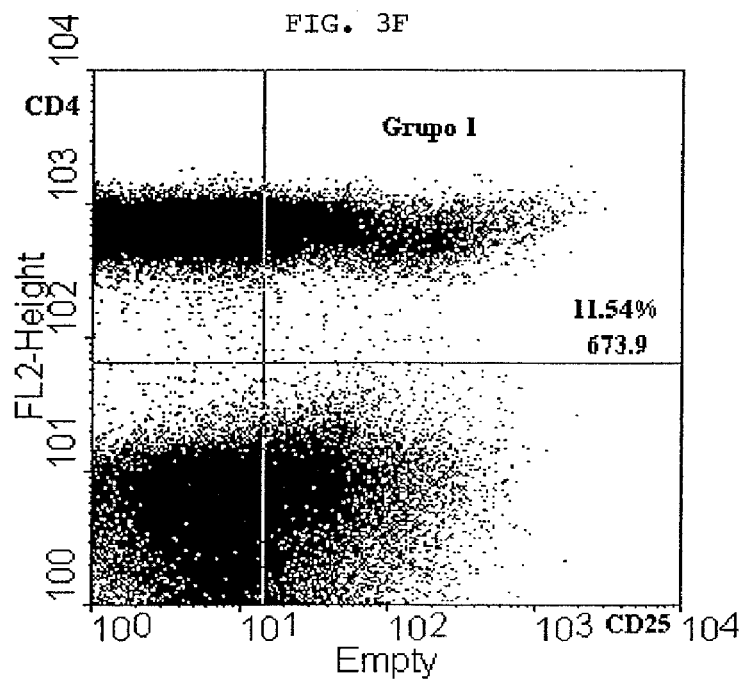
Figure 3G:
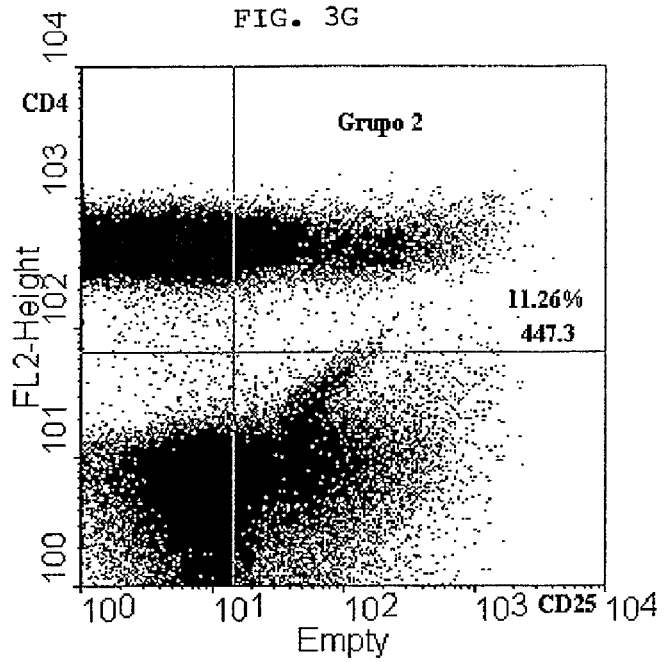
Figure 3H:
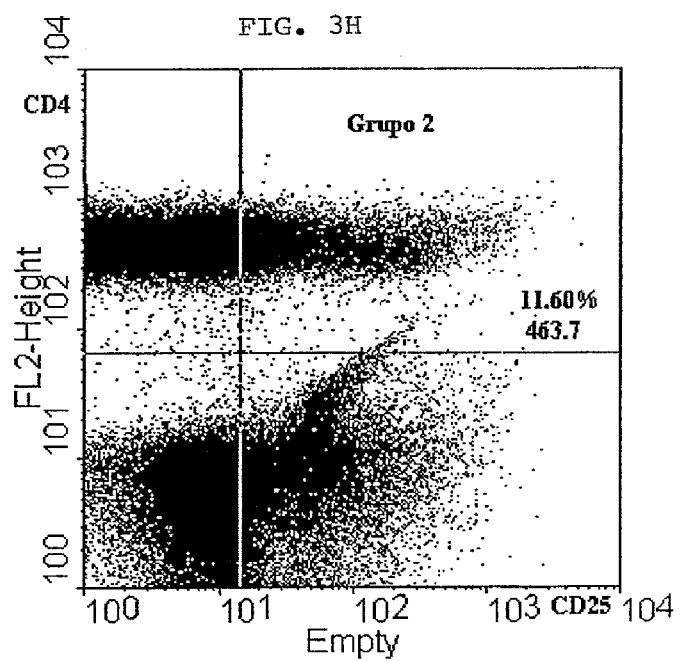
Figure 3I:
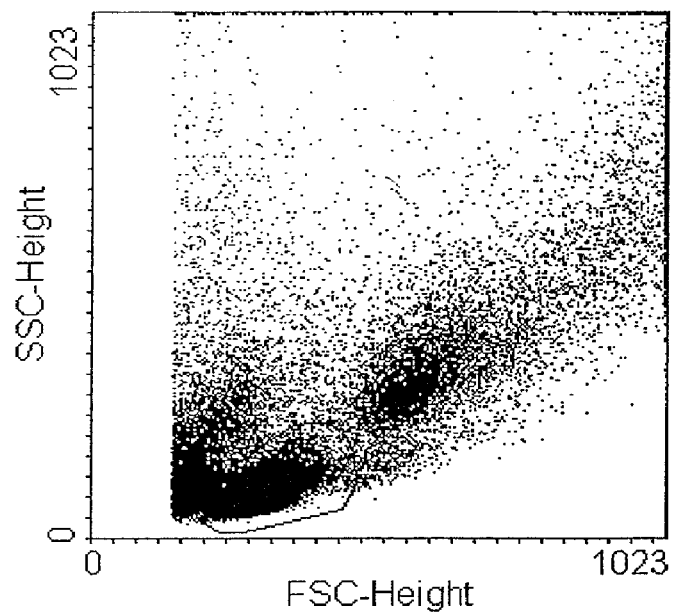
Figure 3J:
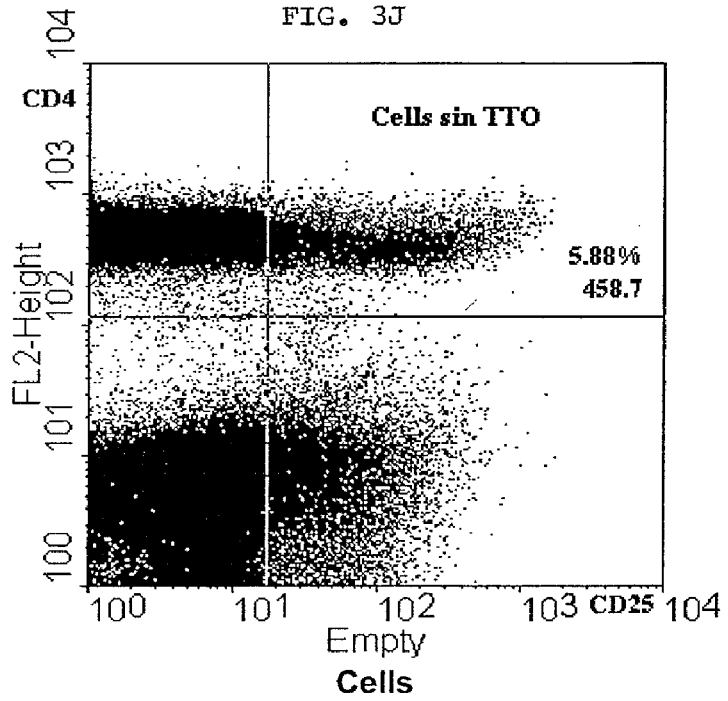
Figure 3K:
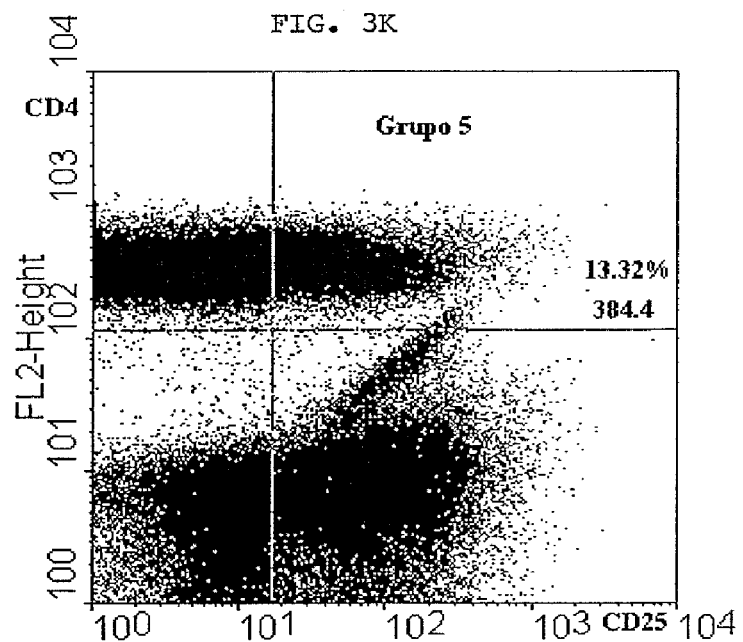
Figure 3L:
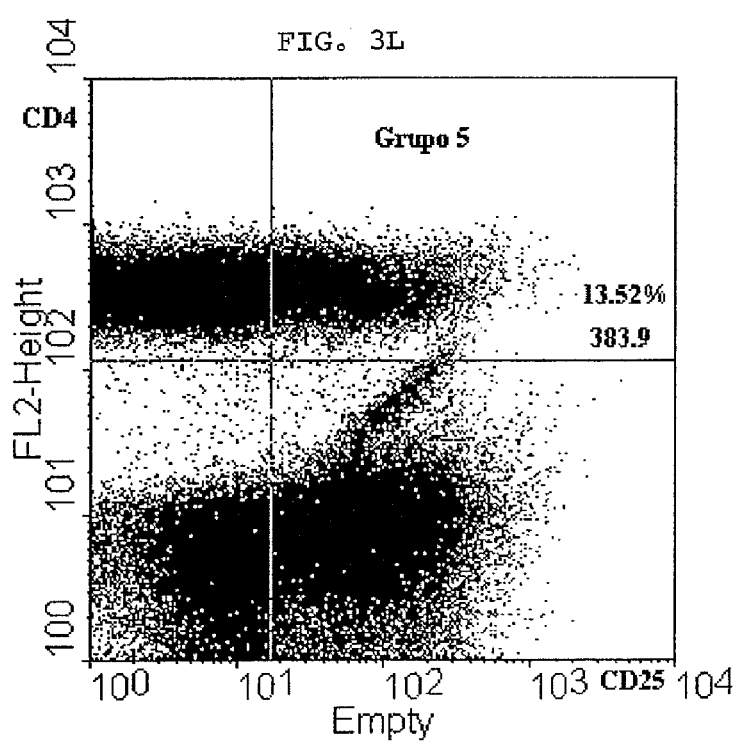
Figure 3M:
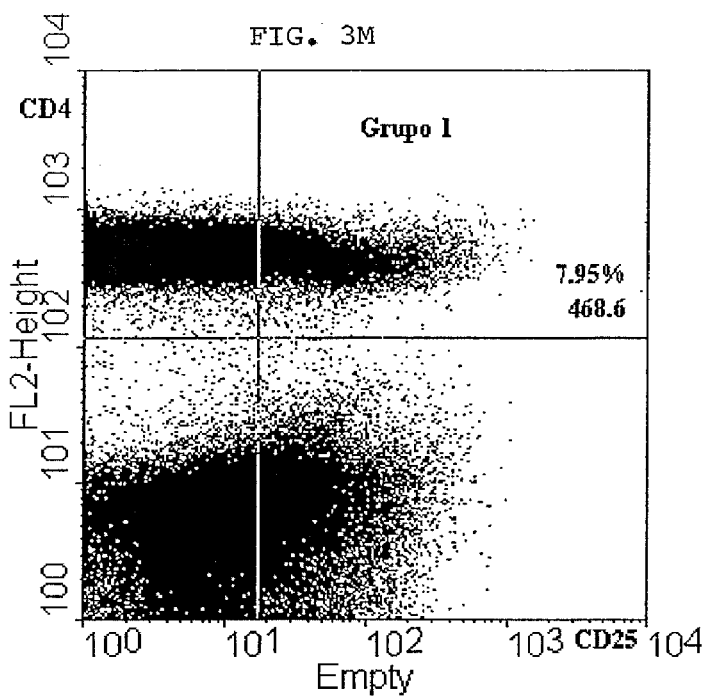
Figure 3N:
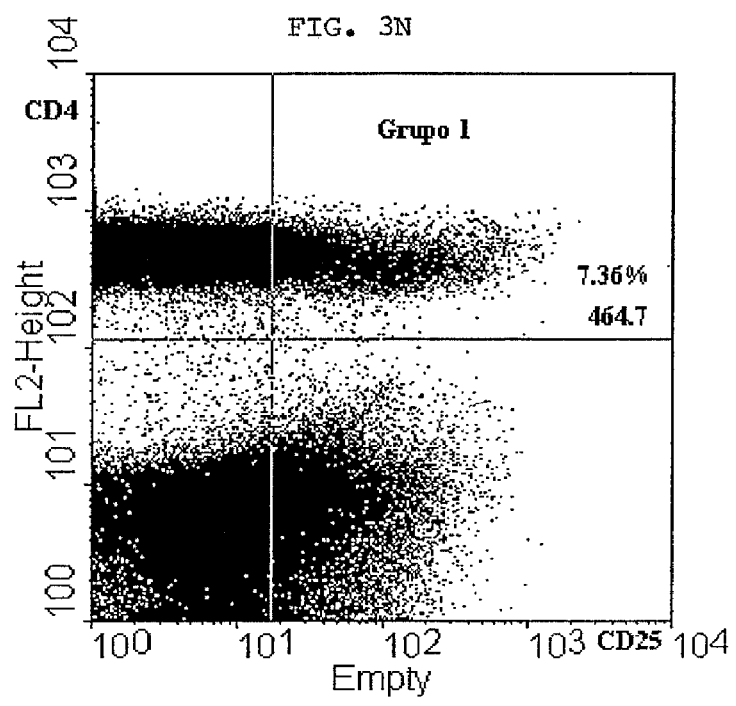
Figure 3Q:
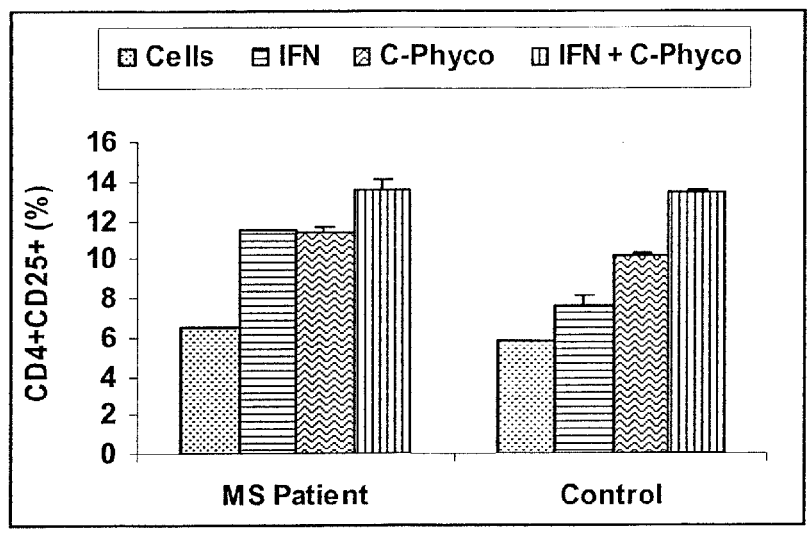
Figure 3R:
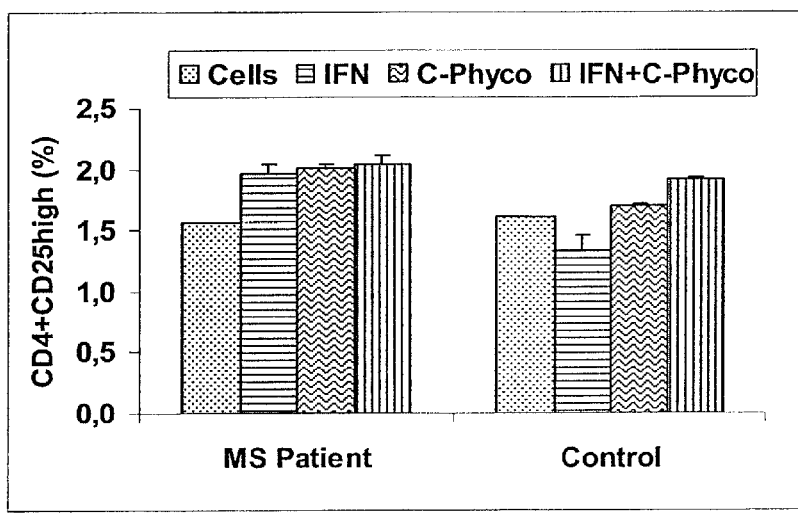
Figure 4A:
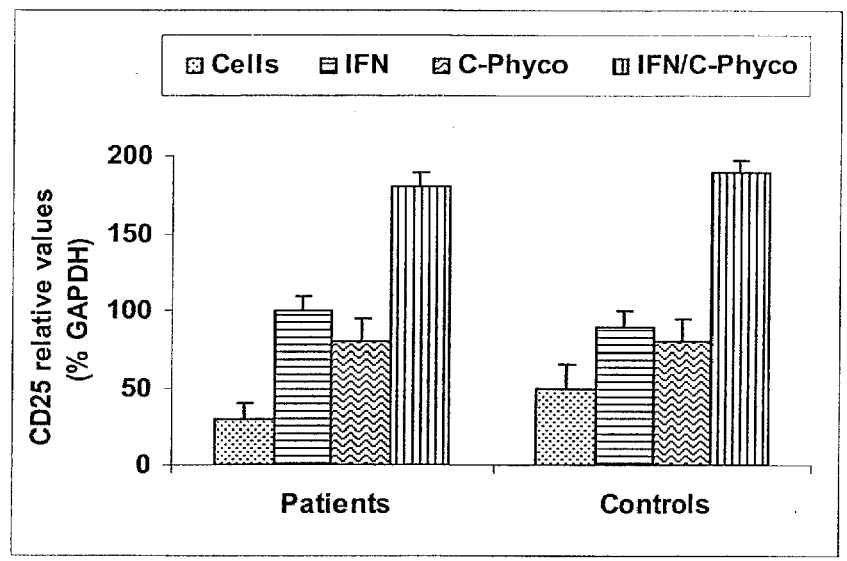
FIG. 4: Effect of the separate treatments and the IFN-α/C-Phyco combination on the expression of genes markers of natural regulatory T cells (A and B) and adaptive regulatory T cells (C and D) by RT-PCR in patients with Rheumatoid Arthritis.
Figure 4B:
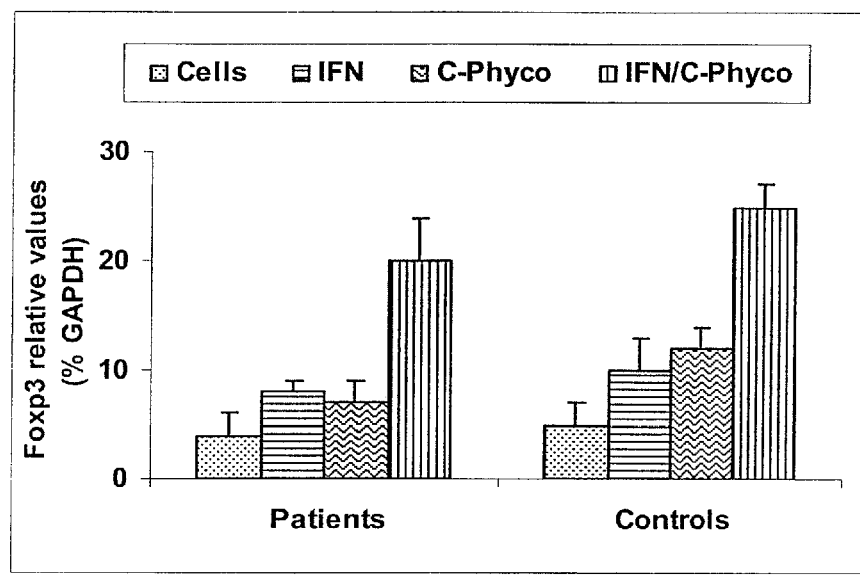
Figure 4C:
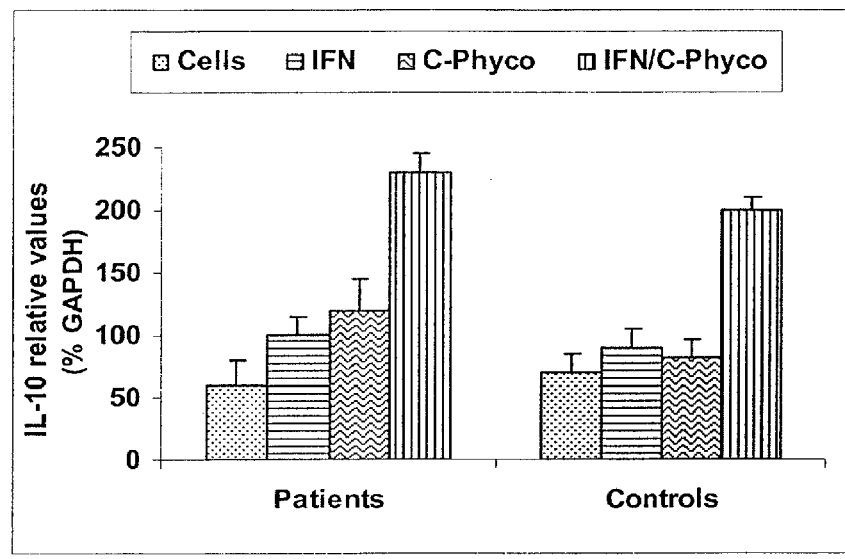
Figure 4D:
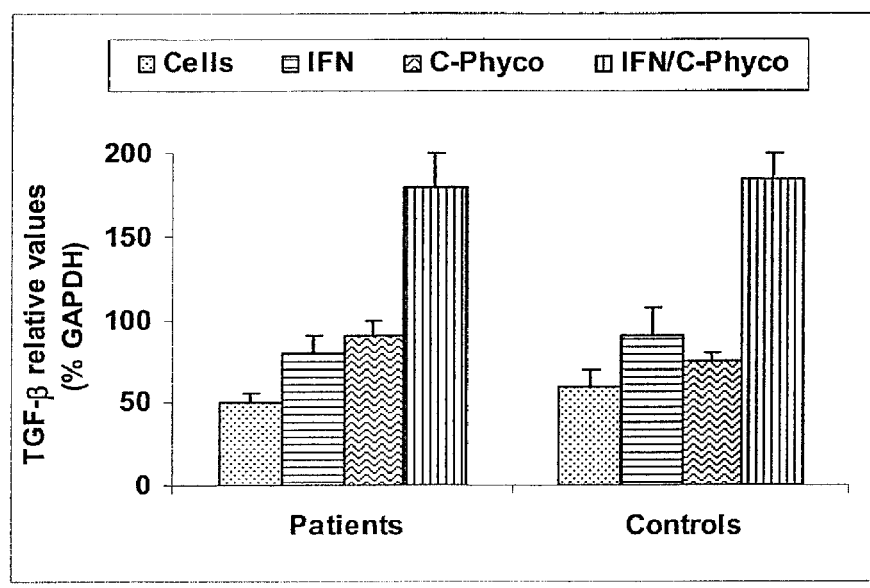
Figure 5A:
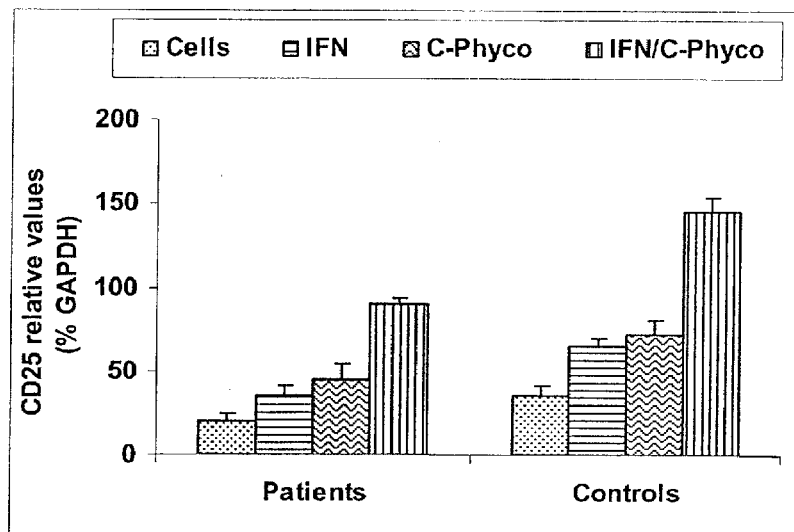
FIG. 5: Effect of the separate treatments and the IFN-α/C-Phyco combination on the expression of genes markers of natural regulatory T cells (A and B) and adaptive regulatory T cells (C and D) for RT-PCR in patients with Bronchial Asthma.
Figure 5B:
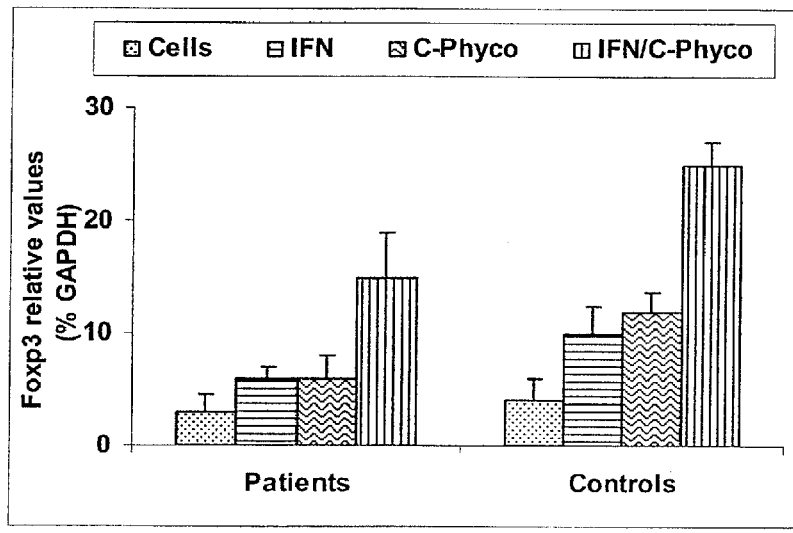
Figure 5C:
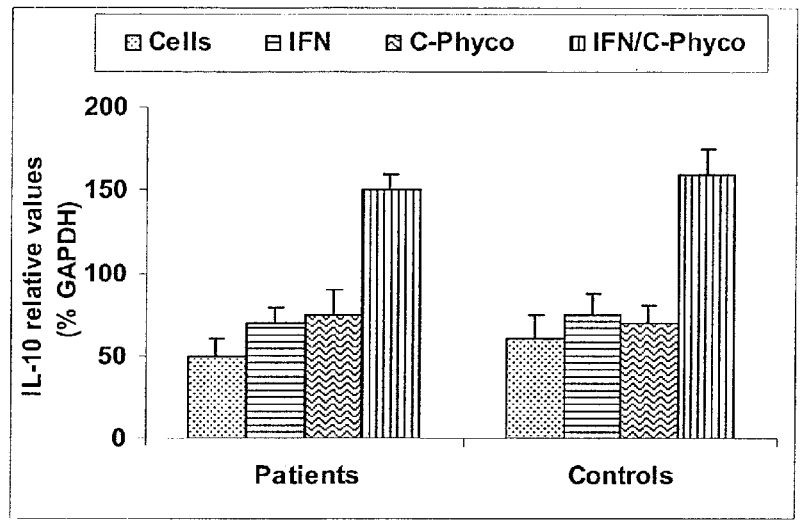
Figure 5D:
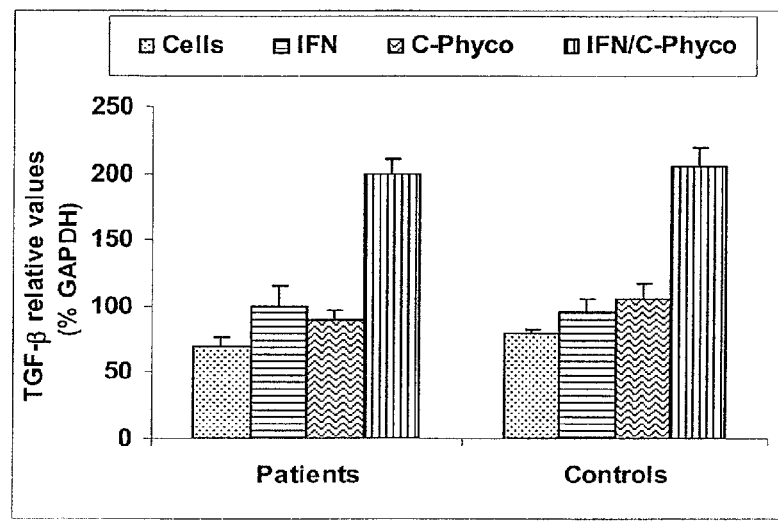

The cells treated with the IFN-α/C-Phyco combination besides showing a statistically significant increase for the CD25 and Foxp3 genes, they showed a positive linear correlation for the CD25/Foxp3 relationship, which was statistically significant with a value of p=0.022, indicating that they are regulatory T cells and non activated T cells (see FIG. 2).

The induction of CD4+CD25+ cells was also demonstrated by Flow Cytometry (FACS) in mononuclear cells of peripheral blood from RRMS patients and controls. For these experiments $10^5$ cells/well were incubated in duplicate per experimental group in 96 well cell culture plates (COSTAR). The experimental groups included: A) Cells alone, B) Cells+5 µM IFN-a2b, C) Cells+20 µM C-Phyco, D) Cells+5 µM IFN-a2b/20 µM C-Phyco. Cells were treated for 72 hours at 37 degrees Celsius and 5% $CO_2$. Afterwards the cells were washed and incubated with the anti-CD4-PE (Serotec) and anti-CD25-Cy5 (Serotec) antibodies and then the readings were made on the FACS.

The results show an induction effect of CD4+CD25+ and CD4+$CD_{25}^{high}$ cells for the separate components and it was even higher for the IFN-α/C-Phyco combination in the patients and controls (the results presented in our invention represent 3 patients and 3 controls). The induction effect of the IFN-α/C-Phyco combination reached the maximum biological values possible. (FIGS. 3A-P and 3Q-R).

Example 4

Evaluation of the Induction Effect of Natural and Adaptive rTc of the IFN-α IFN-α/C-Phyco Combination and its Separate Active Principles in Mononuclear Cells of Patients With Rheumatoid Arthritis For the evaluation of the effect of rTc on the markers genes the procedure is the same as that described in the above section using 6 patients and 6 controls.

The results are expressed as explained in the RT-PCR section. As shown in FIG. 4, there is an induction effect of rTc expressed by an increase in its markers when the cells are treated either with the separate active principles or with the combination. The induction effect was observed in all cases, showing statistical significance with a value of p=0.016 (paired t) for CD25 (A), p=0.029 (paired t) for Foxp3 (B), p=0.034 (paired t) for IL-10 (C) and p=0.028 (Wilcoxon) for TGF-β (D) in the treatment with the IFN-α/C-Phyco combination. Although the cells treated with the separate active principles showed an rTc induction effect, the difference was not statistically significant for any of the genes evaluated, while a synergic effect of the IFN-α/C-Phyco combination was always observed in patients as well in the controls.

Example 5

Evaluation of the Effect of Natural and Adaptive rTc Induction of the IFN-α/C-Phyco Combination and the Separate Active Principles in Mononuclear Cells of Patients With Bronchial Asthma The experimental variants were those explained above, as well as the RT-PCR procedure and data processing. Six patients and 6 controls were studied.

Results show an induction effect of both the natural and induced rTc in the patients and controls, which is statistically significant for the cells treated with the IFN-α/C-Phyco combination showing a value of p=0.012 (paired t test) for CD25, p=0.009 (paired t test) for Foxp3, p=0.037 (paired t test) for IL-10 and p=0.021 (Wilcoxon) for TGF-β (FIG. 5).

Example 6

Evaluation of the Anti-Tumoral Effect of the IFN-α/C-Phyco Combination and its Separate Active Principles in Tumor Cell Lines The anti-tumoral activity of the IFN-α/C-Phyco combination, as well as its independent components was expressed through the evaluation of the anti-proliferative and cytotoxic activity and the induction of apoptosis in tumor cells.

For the evaluation of the anti-proliferative and cytotoxic activity of the IFN-α/C-Phyco combination and of its separate active principles several human tumor cell lines were used in-vitro: HeLa (human cervical carcinoma), HepG2 (human hepatocarcinoma), A375 (human melanoma), HL60 (human pro-myelocitic leukemia), K562 (human erythroleukemia), PBMC (mononuclear cells from peripheral blood). The cells were cultivated in 96 well plates (Costar), a total of 2000 cells/well for the tumor cell lines and 20,000 cells/well for the BPMC. The inhibition of cell proliferation was evaluated through the 3-(4,5-dimethylthiazol-2-yl)-2,5diphenyltetrazolium bromide assay (MTT; Sigma Chemical Co., St Louis, Mo., USA) as described by Mosmann et al. (Mosmann T. Rapid colorimetric assay for cellular growth and survival: application to proliferation and cytotoxicity assays. (1983) J IMMUNOL METHODS 65: 55-63), with modifications. Every cell line evaluated was cultivated to achieve the total amount of cells referred to above, in the appropriate culture medium for each cell line of which 100 µl/well were added and they were incubated for 24 hours at 37 degrees Celsius and 5% CO2. After this time, the culture medium was replaced by another culture medium containing the different treatments in duplicate: A) Cells alone, B) Cells+5 µM IFNα-2b, C) Cells+20 µM C-Phyco, D) Cells+5 µM IFNα-2b/20 µM C-Phyco. The treated cells were incubated for another 48 hours under the same conditions. Afterwards, MTT was added and the soluble products were read in a plate reader at 540 nm (Multiscan, Titertek).

Results are shown in Table 4. They are expressed as % of inhibition of cell proliferation, compared to the control with cells alone. The inhibition of cell proliferation was observed for all tumor cell lines and less for the BPMC. A synergic effect of the IFN-α/C-Phyco combination was also detected in the inhibition of cell proliferation compared to the separate active principles. This effect was greater for the HeLa cell lines and A375.

Figure 6:
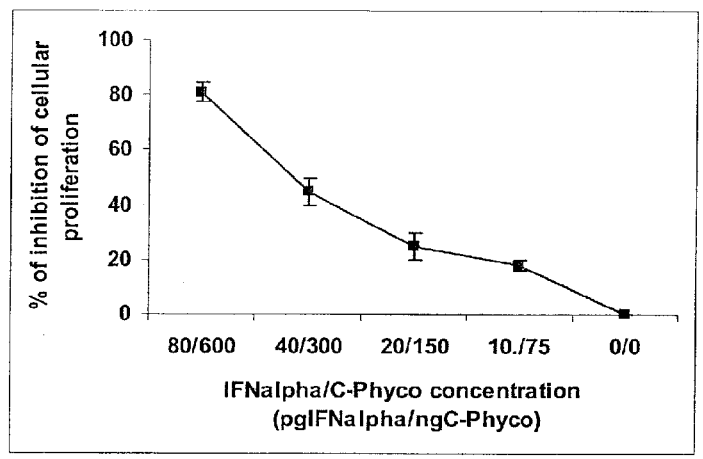
FIG. 6: Dose-response effect of the IFN-α/C-Phyco combination on the inhibition of proliferation in the HeLa cell line.

FIG. 6 shows the dose-dependent effect of the IFN-α/C-Phyco combination on the inhibition of proliferation in the HeLa cell line.

TABLE 4

Evaluation of the antiproliferative activity of the IFN-α/C-Phyco combination and their separate active principles in tumor cell lines.

| Cell lines | IFN-α | C-Phyco | IFN-α/C-Phyco |
|---|---|---|---|
| HeLa | 40% | 30% | 80% |
| HepG2 | 30% | 30% | 70% |
| A375 | 30% | 40% | 75% |
| K562 | 20% | 30% | 60% |
| PBMC | 20% | 20% | 50% |

The induction of apoptosis activity by the IFN-α/C-Phyco combination and its separate active principles were also evaluated through their effect on the expression of the COX-2 and Bcl-2 genes by RT-PCR and the expression of the cytochrome-C protein by Western-Blot.

To carry out the RT-PCR we used a Perkin Elmer Kit. In each case we started off with 1 µg of total RNA/experimental variable that was extracted from the K562 cell line. The RT reaction was carried out in a total volume of 20 µl that was later divided into 2 PCR reactions of 10 µl each. The GAPDH was used as the gene of constitutive expression in order to normalize the relative values obtained with the Molecular Analysis software from the densitometry of agarose gels where the PCR products were separated.

The effect of the IFN-α/C-Phyco combination was assessed by the expression of the genes of COX-2 and Bcl-2, for which $10^5$ cells/experimental variable were cultured for 8 hours using: A) Cells alone, B) Cells+5 µM IFNα-2b, C) Cells+20 µM C-Phyco, D) Cells+5 µM IFNα-2b/20 µM C-Phyco in RPMI 1640 media/10% of serum fetal bovine without the complement.

Figure 7A:
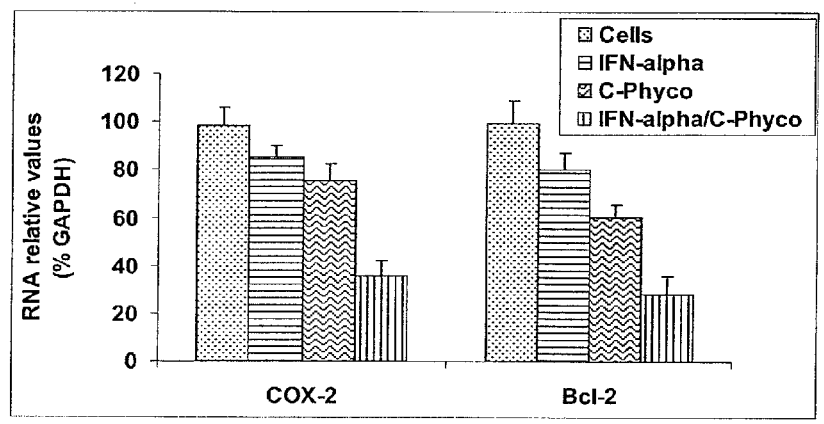
FIG. 7: A) Effect of the IFN-α/C-Phyco combination and the separate active principles on the expression of the COX-2 and Bcl-2 genes in the K562 cell line. B) Time-dependent effect of the IFN-α/C-Phyco combination on the expression of the COX-2 and Bcl-2 genes in the K562 cell line.

Results show an inhibitory effect of the separate active principles as well as a synergic inhibitory effect of the IFN-α/C-Phyco combination, which was statistically significant with a value of p=0.011 (ANOVA. Cells alone vs the IFN-α/C-Phyco Combination) for the expression of the COX-2 gene and p=0.009 (ANOVA Cells alone vs Combination IFN-α/C-Phyco) for the Bcl-2 gene, which are well-known anti-apoptotic molecules (FIG. 7A).

Furthermore, we demonstrated a time-dependent effect of the IFN-α/C-Phyco combination on the inhibition of genes COX-2 and Bcl-2 in the K562 cell line. (FIG. 7B).

One of the pathways for the induction of apoptosis involves the union of Fas to FasL. Fas can be regulated positively by IFN-α, (Gordon M, Marley S B, Lewis J L, et al.) The treatment with interferon-alpha preferentially reduces the capacity for amplification of the granulocyte-macrophage progenitors (CFU-GM) from patients with chronic myeloid leukemia but spares normal CFU-GM. (1998) J Clin Invest 102:710-715) this event promotes the apoptosis mediated by Fas (Selleri C M J, Pane F, Luciano L, et al. Fas-mediated modulation of bcr/abl in chronic myeloid leukemia results in differential effects on apoptosis (1998) Blood 92: 981-989), in our invention we studied whether the IFN-α/C-Phyco combination had a positive regulator effect of Fas compared to IFN-α alone. The experimental variants carried out were explained in the previous example. $10^5$ cells/experimental variant of the K562 cell line, were cultured for 4 hours with the different treatments and the expression level of Fas was measured by RT-PCR as explained in previous sections. The results are shown in FIG. 8 where a statistically significant stimulation effect is observed for IFN-α on the Fas gene with a value of p=0.042 (ANOVA Cells alone vs IFN-α). C-Phyco regulated Fas positively as well, but the difference was not statistically significant and a synergic positive regulation effect of Fas was observed by the IFN-α/C-Phyco combination in this cell line with a value of p=0.009 (ANOVA Cells alone vs IFN-α/C-Phyco combination).

Western blot was used for the evaluation of the IFN-α/C-Phyco combination effect on the cytochrome-C expression at the protein level (Chandra J, et al. Proteasoma inhibitors induce apoptosis in glucocorticoid-resistant chronic lymphocytic leukemia lymphocytes. (1998) Blood 92: 4220). 5 µg of proteins/experimental variable, from K562 cells treated as explained above were cultured for 24 hours and separated by SDS-PAGE electrophoresis in a 15% acrylamide gel. The proteins were later transferred to a nitrocellulose membrane where the specific protein was detected with the use of an anti-cytochrome-C murine monoclonal antibody.

Figure 9:
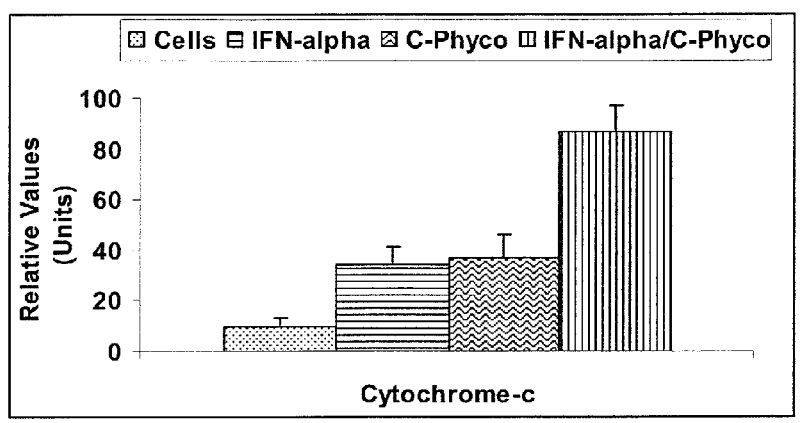
FIG. 9: Effect of the separate active principles and of the IFN-α/C-Phyco combination on the expression of the cytochrome-C protein.

The results are shown in FIG. 9 where it is observed that the IFN-α/C-Phyco combination had an inductive synergic effect, with a statistically significant ANOVA (Cells single vs Combination IFN-α/C-Phyco) p=0.006 on cytochrome-C expression, making it possible for this to be a mediator of the apoptotic effect induced by the IFN-α/C-Phyco combination in K562 cells.

The p53 and p21 proteins are essential for maintaining the arrest of the cellular cycle in phase G2/M and the apoptosis following DNA damage.

An ELISA was used to detect the expression of p53 and p21 proteins (Molecular Roche Biochemical, Germany for p53 and Calbiochem, Cambridge, Mass., USES for p21). The cells were treated with the 30 ng IFNα-2b/50 μM C-Phyco combination or the independent components at the concentrations mentioned above for the experiments shown in FIG. 7A and at 6, 12, 24 and 48 hours for the experiments that are shown in the FIG. 7B. Samples were added with the same amount of protein with the specific biotinilated antibody in 96 well plates, coated with anti-p53 or anti-p21 monoclonal antibodies. After 2 hours of incubation at room temperature the streptavidin-peroxidase conjugate was added. The absorbance was measured at 450 nm and the concentrations were determined by the extrapolation of the standard curve of both proteins of known concentrations.

Figure 10A:
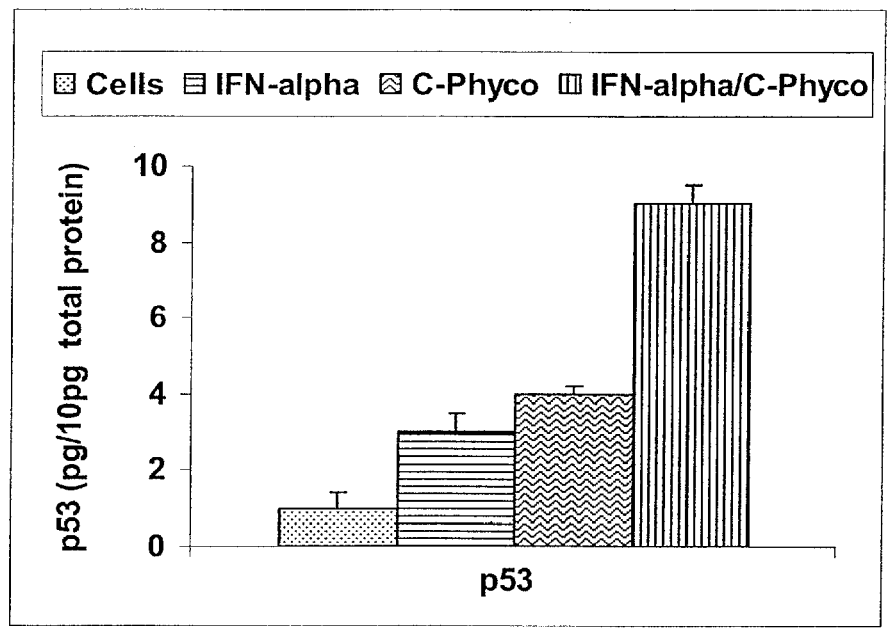
FIG. 10: Effect of the IFN-α/C-Phyco combination and the separate active principles on the levels of proteins p53 (A) and p21 (B) quantified by ELISA HepG2 cells.
Figure 10B:
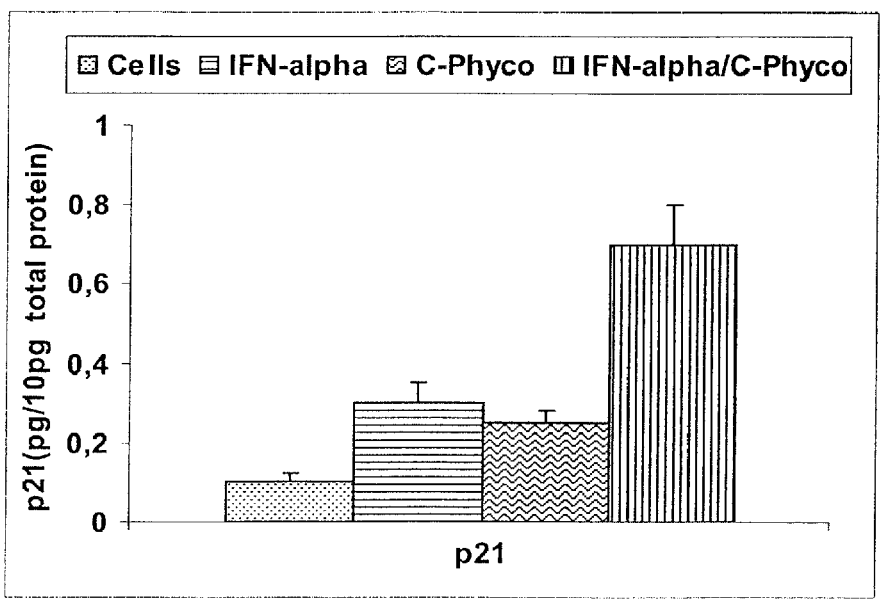

In our invention a statistically significant synergic effect of the IFN-α/C-Phyco combination compared to its independent components is shown where $p=0.026$ for the induction of the p53 protein and $p=0.041$ (ANOVA Cells alone vs Combination IFN-α/C-Phyco) for the levels of expression of the p21 protein detected by ELISA in the HepG2 line of human hepatocarcinoma (FIG. 10).

Figure 11A:
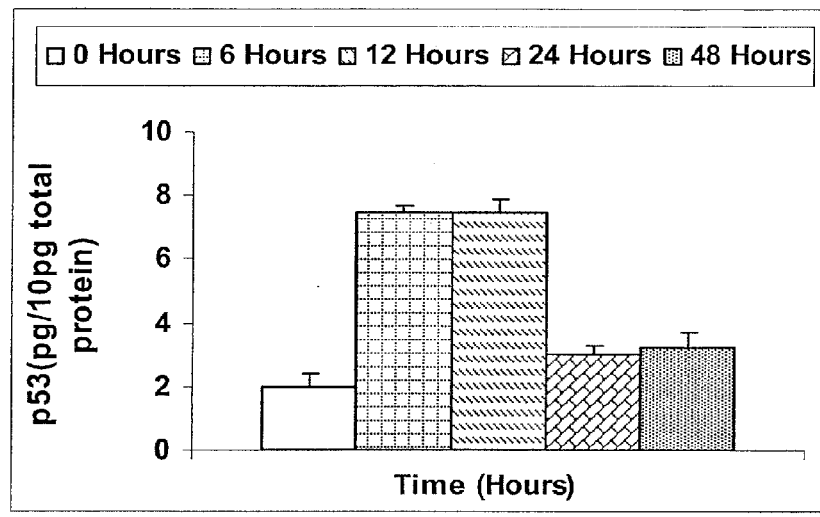
FIG. 11: IFN-α/C-Phyco combination kinetics on the levels of proteins p53 (A) and p21 (B) quantified by ELISA in the HepG2 cell line.

The levels of the p53 protein in the cells treated with the IFN-α/C-Phyco combination (FIG. 11A) after a 6 hour treatment were 4 times higher than when the cells were alone and they remained up-regulated after treating for 12 hours with the combination. These results suggest that the increase in the p53 protein expression may have an important role in the apoptosis of HepG2 cells.

Figure 11B:
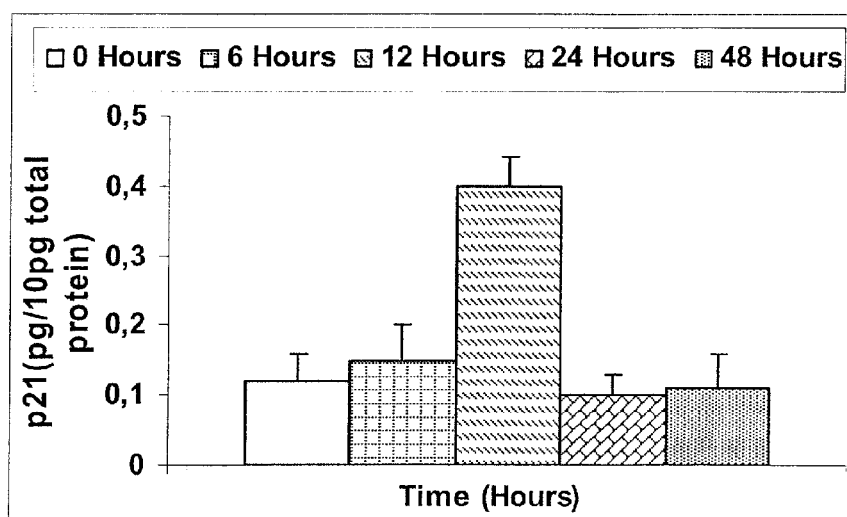

Apoptosis induction has been associated with the negative regulation of target genes that are downstream from the signaling cascade involving p53 as in the gene that codes for the p21 protein. In our invention showed a time dependent effect of the IFN-α/C-Phyco combination on the positive regulation of the expression of the p21 protein. This increase took place after a 12 hour treatment of the cells with the IFN-α/C-Phyco combination (FIG. 11B). The HepG2 cells treated with the combination for 12 hours increased the expression of the p21 protein 4 times.

The expression peak of p53 (6 hours) was earlier than the expression peak of the p21 protein (12 hours), suggesting the possible role of the p53 performing over p21 in the signal transduction mechanism for apoptosis induced by treating cells with the IFN-α/C-Phyco combination.

The invention claimed is:

1. A method for treatment of multiple sclerosis, said method comprising administering to an individual an effective amount of interferon (IFN) alpha and C-Phycocyanin (C-Pc) as active components.

2. A treatment method according to claim 1, wherein the active components are administered to an individual separately or as a pharmaceutical composition.

3. A treatment method according to claim 1, wherein the active components are administered by different routes to an individual.

4. A treatment method according to claim 1, wherein the components are administered through parenteral or oral routes.

5. A treatment method according to claim 1, wherein said treatment reduces the number of relapses.

6. A treatment method according to claim 4, wherein said parenteral administration is selected from the group consisting of intramuscular, intravenous, subcutaneous, nasal, and intrathecal.

* * * * *

UNITED STATES PATENT AND TRADEMARK OFFICE
CERTIFICATE OF CORRECTION

PATENT NO. : 8,110,182 B2
APPLICATION NO. : 12/091776
DATED : February 7, 2012
INVENTOR(S) : Giselle Penton Rol et al.

It is certified that error appears in the above-identified patent and that said Letters Patent is hereby corrected as shown below:

IN THE SPECIFICATIONS:

Column 8, line 46

Now reads: "J Immunol 65:7300-7307";

Should read: -- J Immunol 165:7300-7307 --.

Column 16, line 66

Now reads: "EH, al.";

Should read: -- EH, et al. --.

Column 24, line 34

Now reads: "It been has";

Should read: -- It has been --.

Column 25, line 52

Now reads: "by C-Fico";

Should read: -- by C-Phyco --.

Column 26, line 37

Now reads: "Japanese Patent Not.";

Should read: -- Japanese Patent No. --.

Column 28, line 26

Now reads: "182: 475-481.";

Should read: -- 182: 475-481). --.

Column 33, line 8

Now reads: "The the";

Should read: -- The --.

Signed and Sealed this
Seventh Day of May, 2013

Teresa Stanek Rea
*Acting Director of the United States Patent and Trademark Office*